US006756481B2

(12) United States Patent
Chirica et al.

(10) Patent No.: US 6,756,481 B2
(45) Date of Patent: Jun. 29, 2004

(54) IL-23 RECEPTOR BINDING COMPOSITIONS

(75) Inventors: Madaline Chirica, Mountain View, CA (US); Robert A. Kastelein, Redwood City, CA (US); Kevin W. Moore, Palo Alto, CA (US); Christi L. Parham, San Francisco, CA (US)

(73) Assignee: Schering Corporation, Kenilworth, NJ (US)

( * ) Notice: Subject to any disclaimer, the term of this patent is extended or adjusted under 35 U.S.C. 154(b) by 150 days.

(21) Appl. No.: 09/853,180

(22) Filed: May 10, 2001

(65) Prior Publication Data

US 2003/0017617 A1 Jan. 23, 2003

Related U.S. Application Data

(60) Provisional application No. 60/203,426, filed on May 10, 2000.

(51) Int. Cl.[7] .............................. C12Q 1/68; C12N 5/06; G01N 33/53; C07K 16/00
(52) U.S. Cl. .................... 530/387.9; 435/334; 435/335; 435/343; 435/975; 435/7.1; 530/350; 530/351; 530/387.1; 530/388.2
(58) Field of Search ................................. 530/350, 351, 530/387.1, 387.9, 388.2; 435/6, 7.1, 334, 335, 343, 975

(56) References Cited

U.S. PATENT DOCUMENTS

2003/0009018 A1 * 1/2003 Maeda et al. .............. 536/23.1

OTHER PUBLICATIONS

Scott, D et. al., The Pendred syndrome gene encodes a chloride–iodide transport protein. (1999), Nature Genetics, vol. 21, pp440–443.*
Ngo et al., 1994, Computational Complexity, Protein Structure prediction, and the Levinthal Paradox, The Protein Folding Problem and Tertiary Structure Prediction, pp. 492–495.*
Wells, Aditivity of Mutational Effects in Proteins, 1990, Biochemistry, vol. 26, No:37 , pp. 8509–8517.*
Kim E. Barrett,. Baillieres Clin Gastroenterol., 10(1):1–15, Mar. 1996. "Cytokines: sources, receptors and signalling".
J. Fernando Bazon, et al., Nature, 379:591, Feb. 15, 1996. "A newly defined interleukin-1?".
J. Briscoe, et al., Philos Trans R Soc Lond B Biol Sci. 351(1336):167–71, Feb. 29, 1996. "JAKs, STATs and signal transduction in response to the interferons and other cytokines".
Irwin M. Chaiken & William V. Williams, Trends Biotechnol., 14(10):369–75, Oct. 1996. "Identifying structure–function relationships in four–helix bundle cytokines: towards de novo mimetics design".

Thomas J. Gonda & Richard J. D'Andrea, Blood, 89(2):355–369, Jan. 15, 1997. "Activating mutations in cytokine receptors: implications for receptor function and role in disease".
Peter C. Heinrich, et al., Biochem J., 334 (Pt 2):297–314, Sep. 1, 1998. "Interleukin 6–type cytokine signalling through the gp130/Jak/STAT pathway".
Jeffrey M. Herz, et al., J Recept Signal Transduct Res., 17(5):671–776, Sep. 1997. "Molecular approaches to receptors as targets for drug discovery".
M. Hibi, et al., GenBank, Accession No. M57230, Jan. 6, 1995. Definition: Human membrane glycoprotein gp130 mRNA, complete cds.
James N. Ihle, et al. Stem Cells, 15 (Suppl 1):105–11, 1997. "Jaks and Stats in cytokine signaling".
David E. Levy, Cytokine Growth Factor Rev., 8(1):81–90, Mar. 1997. "The house that JAK/STAT built".
S. Lok, et al., Database EMBL Online!, Accession No. AF178684, Sep. 10, 1999. Definition: Homo sapiens class I cytokine receptor (zcytor5) mRNA, complete cds.
Neela Patel, et al., J Biol Chem., 271(48):30386–30391, Nov. 29, 1996. "Functional replacement of cytokine receptor extracellular domains by leucine zippers".
David H. Presky, et al., Proc. Natl. Acad. Sci. USA, 93:14002–14007, Nov. 1996. "A functional interleukin 12 receptor complex is composed of two b–type cytokine receptor subunits".
D. H. Presky, et al., GenBank, Accession No. U64198, Nov. 28, 2000. Definition: Human IL–12 receptor beta2 mRNA, complete cds.
Olli Silvennoinen, et al., APMIS, 105(7):497–509, Jul. 1997. "Cytokine receptor signal transduction through Jak tyrosine kinases and Stat transcription factors".
R.H. Waterson, Database EMBL Online!, Accession No., AC26054, Mar. 20, 2000. Definition: Homo sapiens chromosome 1 clone RP11–131015, working draft sequence, 26 unordered pieces.
Linda A. Winston & Tony Hunter, Current Biology, 6(6):668–671, Jun. 1, 1996. "Intracellular signalling: Puttig JAKs on the kinase MAP".

* cited by examiner

Primary Examiner—Lorraine Spector
Assistant Examiner—Jegatheesan Seharaseyon
(74) Attorney, Agent, or Firm—Sheela Mohan-Peterson; Edwin P. Ching

(57) ABSTRACT

Nucleic acids encoding mammalian, e.g., primate, receptors, purified receptor proteins and fragments thereof. Antibodies, both polyclonal and monoclonal, are also provided. Methods of using the compositions for both diagnostic and therapeutic utilities are described.

5 Claims, No Drawings

SEQUENCE LISTING

<160> NUMBER OF SEQ ID NOS: 4

<210> SEQ ID NO 1
<211> LENGTH: 2859
<212> TYPE: DNA
<213> ORGANISM: Homo sapiens
<220> FEATURE:
<221> NAME/KEY: CDS
<222> LOCATION: (119)..(2005)
<223> OTHER INFORMATION:

<400> SEQUENCE: 1

```
gtggtacggg aattccattg tgttgggcag ccaacaaggg tggcagcctg gctctgaagt      60
ggaattatgt gcttcaaaca ggttgaaaga gggaaacagt cttttcctgc ttccagac       118 atg aat cak gtc act att caa tgg gat gca gta ata gcc ctt tac ata      166
Met Asn Xaa Val Thr Ile Gln Trp Asp Ala Val Ile Ala Leu Tyr Ile
1               5                   10                  15 ctc ttc agc tgg tgt cat gga gga att aca aat ata aac tgc tct ggc      214
Leu Phe Ser Trp Cys His Gly Gly Ile Thr Asn Ile Asn Cys Ser Gly
            20                  25                  30 cac atc tgg gta gaa cca gcc aca att ttt aag atg ggt atg aat atc      262
His Ile Trp Val Glu Pro Ala Thr Ile Phe Lys Met Gly Met Asn Ile
        35                  40                  45 tct ata tat tgc caa gca gca att aag aac tgc caa cca agg aaa ctt      310
Ser Ile Tyr Cys Gln Ala Ala Ile Lys Asn Cys Gln Pro Arg Lys Leu
    50                  55                  60 cat ttt tat aaa aat ggc atc aaa gaa aga ttt caa atc aca agg att      358
His Phe Tyr Lys Asn Gly Ile Lys Glu Arg Phe Gln Ile Thr Arg Ile
65                  70                  75                  80 aat aaa aca aca gct cgg ctt tgg tat aaa aac ttt ctg gaa cca cat      406
Asn Lys Thr Thr Ala Arg Leu Trp Tyr Lys Asn Phe Leu Glu Pro His
                85                  90                  95 gct tct atg tac tgc act gct gaa tgt ccc aaa cat ttt caa gag aca      454
Ala Ser Met Tyr Cys Thr Ala Glu Cys Pro Lys His Phe Gln Glu Thr
            100                 105                 110 ctg ata tgt gga aaa gac att tct tct gga tat ccg cca gat att cct      502
Leu Ile Cys Gly Lys Asp Ile Ser Ser Gly Tyr Pro Pro Asp Ile Pro
        115                 120                 125 gat gaa gta acc tgt gtc att tat gaa tat tca ggc aac atg act tgc      550
Asp Glu Val Thr Cys Val Ile Tyr Glu Tyr Ser Gly Asn Met Thr Cys
    130                 135                 140 acc tgg aat gct rgg aag ctc acc tac ata gac aca aaa tac gtg gta      598
Thr Trp Asn Ala Xaa Lys Leu Thr Tyr Ile Asp Thr Lys Tyr Val Val
145                 150                 155                 160 cat gtg aag agt tta gag aca gaa gaa gag caa cag tat ctc acc tca      646
His Val Lys Ser Leu Glu Thr Glu Glu Glu Gln Gln Tyr Leu Thr Ser
                165                 170                 175 agc tat att aac atc tcc act gat tca tta caa ggt ggc aag aag tac      694
Ser Tyr Ile Asn Ile Ser Thr Asp Ser Leu Gln Gly Gly Lys Lys Tyr
            180                 185                 190 ttg gtt tgg gtc caa gca gca aac gca cta ggc atg gaa gag tca aaa      742
Leu Val Trp Val Gln Ala Ala Asn Ala Leu Gly Met Glu Glu Ser Lys
        195                 200                 205 caa ctg caa att cac ctg gat gat ata gtg ata cct tct gca gcc gtc      790
Gln Leu Gln Ile His Leu Asp Asp Ile Val Ile Pro Ser Ala Ala Val
    210                 215                 220 att tcc agg gct gag act ata aat gct aca gtg ccc aag acc ata att      838
Ile Ser Arg Ala Glu Thr Ile Asn Ala Thr Val Pro Lys Thr Ile Ile
225                 230                 235                 240
```

```
tat tgg gat agt caa aca aca att gaa aag gtt tcc tgt gaa atg aga      886
Tyr Trp Asp Ser Gln Thr Thr Ile Glu Lys Val Ser Cys Glu Met Arg
                245                 250                 255 tac aag gct aca aca aac caa act tgg aat gtt aaa gaa ttt gac acc      934
Tyr Lys Ala Thr Thr Asn Gln Thr Trp Asn Val Lys Glu Phe Asp Thr
            260                 265                 270 aat ttt aca tat gtg caa cag tca gaa ttc tac ttg gag cca aac att      982
Asn Phe Thr Tyr Val Gln Gln Ser Glu Phe Tyr Leu Glu Pro Asn Ile
        275                 280                 285 aag tac gta ttt caa gtg aga tgt caa gaa aca ggc aaa agg tac tgg     1030
Lys Tyr Val Phe Gln Val Arg Cys Gln Glu Thr Gly Lys Arg Tyr Trp
    290                 295                 300 cag cct tgg agt tca ccg ttt ttt cat aaa aca cct gaa aca gtt ccc     1078
Gln Pro Trp Ser Ser Pro Phe Phe His Lys Thr Pro Glu Thr Val Pro
305                 310                 315                 320 cag gtc aca tca aaa gca ttc caa cat gac aca tgg aat tct ggg cta     1126
Gln Val Thr Ser Lys Ala Phe Gln His Asp Thr Trp Asn Ser Gly Leu
                325                 330                 335 aca gtt gct tcc atc tct aca ggg cac ctt act tct gac aac aga gga     1174
Thr Val Ala Ser Ile Ser Thr Gly His Leu Thr Ser Asp Asn Arg Gly
            340                 345                 350 gac att gga ctt tta ttg gga atg atc gtc ttt gct gtt atg ttg tca     1222
Asp Ile Gly Leu Leu Leu Gly Met Ile Val Phe Ala Val Met Leu Ser
        355                 360                 365 att ctt tct ttg att ggg ata ttt aac aga tca ttc cga act ggg att     1270
Ile Leu Ser Leu Ile Gly Ile Phe Asn Arg Ser Phe Arg Thr Gly Ile
    370                 375                 380 aaa aga agg atc tta ttg tta ata cca aag tgg ctt tat gaa gat att     1318
Lys Arg Arg Ile Leu Leu Leu Ile Pro Lys Trp Leu Tyr Glu Asp Ile
385                 390                 395                 400 cct aat atg aaa aac agc aat gtt gtg aaa atg cta cag gaa aat agt     1366
Pro Asn Met Lys Asn Ser Asn Val Val Lys Met Leu Gln Glu Asn Ser
                405                 410                 415 gaa ctt atg aat aat aat tcc agt gag cag gtc cta tat gtt gat ccc     1414
Glu Leu Met Asn Asn Asn Ser Ser Glu Gln Val Leu Tyr Val Asp Pro
            420                 425                 430 atg att aca gag ata aaa gaa atc ttc atc cca gaa cac aag cct aca     1462
Met Ile Thr Glu Ile Lys Glu Ile Phe Ile Pro Glu His Lys Pro Thr
        435                 440                 445 gac tac aag aag gag aat aca gga ccc ctg gag aca aga gac tac ccg     1510
Asp Tyr Lys Lys Glu Asn Thr Gly Pro Leu Glu Thr Arg Asp Tyr Pro
    450                 455                 460 caa aac tcg cta ttc gac aat act aca gtt gta tat att cct gat ctc     1558
Gln Asn Ser Leu Phe Asp Asn Thr Thr Val Val Tyr Ile Pro Asp Leu
465                 470                 475                 480 aac act gga tat aaa ccc caa att tca aat ttt ctg cct gag gga agc     1606
Asn Thr Gly Tyr Lys Pro Gln Ile Ser Asn Phe Leu Pro Glu Gly Ser
                485                 490                 495 cat ctc agc aat aat aat gaa att act tcc tta aca ctt aaa cca cca     1654
His Leu Ser Asn Asn Asn Glu Ile Thr Ser Leu Thr Leu Lys Pro Pro
            500                 505                 510 gtt gat tcc tta gac tca gga aat aat ccc agg tta caa aag cat cct     1702
Val Asp Ser Leu Asp Ser Gly Asn Asn Pro Arg Leu Gln Lys His Pro
        515                 520                 525 aat ttt gct ttt tct gtt tca agt gtg aat tca cta agc aac aca ata     1750
Asn Phe Ala Phe Ser Val Ser Ser Val Asn Ser Leu Ser Asn Thr Ile
    530                 535                 540 ttt ctt gga gaa tta agc ctc ata tta aat caa gga gaa tgc agt tct     1798
Phe Leu Gly Glu Leu Ser Leu Ile Leu Asn Gln Gly Glu Cys Ser Ser
```

-continued

```
          545                 550                 555                 560 cct gac ata caa aac tca gta gag gag gaa acc acc atg ctt ttg gaa      1846
Pro Asp Ile Gln Asn Ser Val Glu Glu Glu Thr Thr Met Leu Leu Glu
                565                 570                 575 aat gat tca ccc agt gaa act att cca gaa cag acc ctg ctt cct gat      1894
Asn Asp Ser Pro Ser Glu Thr Ile Pro Glu Gln Thr Leu Leu Pro Asp
            580                 585                 590 gaa ttt gtc tcc tgt ttg ggg atc gtg aat gag gag ttg cca tct att      1942
Glu Phe Val Ser Cys Leu Gly Ile Val Asn Glu Glu Leu Pro Ser Ile
        595                 600                 605 aat act tat ttt cca caa aat att ttg gaa agc cac ttc aat agg att      1990
Asn Thr Tyr Phe Pro Gln Asn Ile Leu Glu Ser His Phe Asn Arg Ile
    610                 615                 620 tca ctc ttg gaa aag tagagctgtg tggtcaaaat caatatgaga aagctgcctt      2045
Ser Leu Leu Glu Lys
625 gcaatctgaa cttgggtttt ccctgcaata gaaattgaat tctgcctctt tttgaaaaaa     2105 atgtattcac atacaaatct tcacatggac acatgttttc atttcccttg gataaatacc    2165 taggtagggg attgctgggc catatgataa gcatatgttt cagttctacc aatcttgttt    2225 ccagagtagt gacatttctg tgctcctacc atcaccatgt aagaattccc gggagctcca    2285 tgccttttta attttagcca ttcttctgcc tmatttctta aaattagaga attaaggtcc    2345 cgaaggtgga acatgcttca tggtcacaca tacaggcaca aaaacagcat tatgtggacg    2405 cctcatgtat ttttttataga gtcaactatt tcctctttat tttccctcat tgaaagatgc   2465 aaaacagctc tctattgtgt acagaaaggg taaataatgc aaaatacctg gtagtaaaat    2525 aaatgctgaa aattttcctt taaaatagaa tcattaggcc aggcgtggtg gctcatgctt    2585 gtaatcccag cactttggta ggctgaggtr ggtggatcac ctgaggtcag gagttcgagt    2645 ccagcctggc caatatgctg aaaccctgtc tctactaaaa ttacaaaaat tagccggcca    2705 tggtggcagg tgcttgtaat cccagctact tgggaggctg aggcaggaga atcacttgaa    2765 ccaggaaggc agaggttgca ctgagctgag attgtgccac tgcactccag cctgggcaac    2825 aagagcaaaa ctctgtctgg aaaaaaaaaa aaaa                                2859
```

<210> SEQ ID NO 2
<211> LENGTH: 629
<212> TYPE: PRT
<213> ORGANISM: Homo sapiens
<220> FEATURE:
<221> NAME/KEY: misc_feature
<222> LOCATION: (3)..(3)
<223> OTHER INFORMATION: The 'Xaa' at location 3 stands for Gln, or
   His.
<220> FEATURE:
<221> NAME/KEY: misc_feature
<222> LOCATION: (149)..(149)
<223> OTHER INFORMATION: The 'Xaa' at location 149 stands for Gly, or
   Arg.

<400> SEQUENCE: 2

```
Met Asn Xaa Val Thr Ile Gln Trp Asp Ala Val Ile Ala Leu Tyr Ile
1               5                   10                  15

Leu Phe Ser Trp Cys His Gly Gly Ile Thr Asn Ile Asn Cys Ser Gly
            20                  25                  30

His Ile Trp Val Glu Pro Ala Thr Ile Phe Lys Met Gly Met Asn Ile
        35                  40                  45

Ser Ile Tyr Cys Gln Ala Ala Ile Lys Asn Cys Gln Pro Arg Lys Leu
    50                  55                  60
```

```
His Phe Tyr Lys Asn Gly Ile Lys Glu Arg Phe Gln Ile Thr Arg Ile
 65                  70                  75                  80

Asn Lys Thr Thr Ala Arg Leu Trp Tyr Lys Asn Phe Leu Glu Pro His
                 85                  90                  95

Ala Ser Met Tyr Cys Thr Ala Glu Cys Pro Lys His Phe Gln Glu Thr
            100                 105                 110

Leu Ile Cys Gly Lys Asp Ile Ser Ser Gly Tyr Pro Pro Asp Ile Pro
        115                 120                 125

Asp Glu Val Thr Cys Val Ile Tyr Glu Tyr Ser Gly Asn Met Thr Cys
    130                 135                 140

Thr Trp Asn Ala Xaa Lys Leu Thr Tyr Ile Asp Thr Lys Tyr Val Val
145                 150                 155                 160

His Val Lys Ser Leu Glu Thr Glu Glu Gln Gln Tyr Leu Thr Ser
                165                 170                 175

Ser Tyr Ile Asn Ile Ser Thr Asp Ser Leu Gln Gly Gly Lys Lys Tyr
            180                 185                 190

Leu Val Trp Val Gln Ala Ala Asn Ala Leu Gly Met Glu Glu Ser Lys
        195                 200                 205

Gln Leu Gln Ile His Leu Asp Asp Ile Val Ile Pro Ser Ala Ala Val
    210                 215                 220

Ile Ser Arg Ala Glu Thr Ile Asn Ala Thr Val Pro Lys Thr Ile Ile
225                 230                 235                 240

Tyr Trp Asp Ser Gln Thr Thr Ile Glu Lys Val Ser Cys Glu Met Arg
                245                 250                 255

Tyr Lys Ala Thr Thr Asn Gln Thr Trp Asn Val Lys Glu Phe Asp Thr
            260                 265                 270

Asn Phe Thr Tyr Val Gln Gln Ser Glu Phe Tyr Leu Glu Pro Asn Ile
        275                 280                 285

Lys Tyr Val Phe Gln Val Arg Cys Gln Glu Thr Gly Lys Arg Tyr Trp
    290                 295                 300

Gln Pro Trp Ser Ser Pro Phe Phe His Lys Thr Pro Glu Thr Val Pro
305                 310                 315                 320

Gln Val Thr Ser Lys Ala Phe Gln His Asp Thr Trp Asn Ser Gly Leu
                325                 330                 335

Thr Val Ala Ser Ile Ser Thr Gly His Leu Thr Ser Asp Asn Arg Gly
            340                 345                 350

Asp Ile Gly Leu Leu Leu Gly Met Ile Val Phe Ala Val Met Leu Ser
        355                 360                 365

Ile Leu Ser Leu Ile Gly Ile Phe Asn Arg Ser Phe Arg Thr Gly Ile
    370                 375                 380

Lys Arg Arg Ile Leu Leu Leu Ile Pro Lys Trp Leu Tyr Glu Asp Ile
385                 390                 395                 400

Pro Asn Met Lys Asn Ser Asn Val Val Lys Met Leu Gln Glu Asn Ser
                405                 410                 415

Glu Leu Met Asn Asn Asn Ser Ser Glu Gln Val Leu Tyr Val Asp Pro
            420                 425                 430

Met Ile Thr Glu Ile Lys Glu Ile Phe Ile Pro Glu His Lys Pro Thr
        435                 440                 445

Asp Tyr Lys Lys Glu Asn Thr Gly Pro Leu Glu Thr Arg Asp Tyr Pro
    450                 455                 460

Gln Asn Ser Leu Phe Asp Asn Thr Thr Val Val Tyr Ile Pro Asp Leu
465                 470                 475                 480
```

-continued

```
Asn Thr Gly Tyr Lys Pro Gln Ile Ser Asn Phe Leu Pro Glu Gly Ser
            485                 490                 495

His Leu Ser Asn Asn Glu Ile Thr Ser Leu Thr Leu Lys Pro Pro
        500                 505                 510

Val Asp Ser Leu Asp Ser Gly Asn Asn Pro Arg Leu Gln Lys His Pro
        515                 520                 525

Asn Phe Ala Phe Ser Val Ser Ser Val Asn Ser Leu Ser Asn Thr Ile
        530                 535                 540

Phe Leu Gly Glu Leu Ser Leu Ile Leu Asn Gln Gly Glu Cys Ser Ser
545                 550                 555                 560

Pro Asp Ile Gln Asn Ser Val Glu Glu Thr Thr Met Leu Leu Glu
        565                 570                 575

Asn Asp Ser Pro Ser Glu Thr Ile Pro Glu Gln Thr Leu Leu Pro Asp
        580                 585                 590

Glu Phe Val Ser Cys Leu Gly Ile Val Asn Glu Glu Leu Pro Ser Ile
        595                 600                 605

Asn Thr Tyr Phe Pro Gln Asn Ile Leu Glu Ser His Phe Asn Arg Ile
        610                 615                 620

Ser Leu Leu Glu Lys
625

<210> SEQ ID NO 3
<211> LENGTH: 918
<212> TYPE: PRT
<213> ORGANISM: Homo sapiens

<400> SEQUENCE: 3

Met Leu Thr Leu Gln Thr Trp Val Val Gln Ala Leu Phe Ile Phe Leu
1               5                   10                  15

Thr Thr Glu Ser Thr Gly Glu Leu Leu Asp Pro Cys Gly Tyr Ile Ser
                20                  25                  30

Pro Glu Ser Pro Val Val Gln Leu His Ser Asn Phe Thr Ala Val Cys
            35                  40                  45

Val Leu Lys Glu Lys Cys Met Asp Tyr Phe His Val Asn Ala Asn Tyr
        50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220
```

-continued

```
Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
            245                 250                 255

Tyr Asn Ile Gln Tyr Arg Thr Lys Asp Ala Ser Thr Trp Ser Gln Ile
                260                 265                 270

Pro Pro Glu Asp Thr Ala Ser Thr Arg Ser Ser Phe Thr Val Gln Asp
            275                 280                 285

Leu Lys Pro Phe Thr Glu Tyr Val Phe Arg Ile Arg Cys Met Lys Glu
290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
            355                 360                 365

Thr Leu Thr Arg Trp Lys Ser His Leu Gln Asn Tyr Thr Val Asn Ala
370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
            420                 425                 430

Phe Pro Lys Asp Asn Met Leu Trp Val Glu Trp Thr Thr Pro Arg Glu
            435                 440                 445

Ser Val Lys Lys Tyr Ile Leu Glu Trp Cys Val Leu Ser Asp Lys Ala
    450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
            515                 520                 525

Lys Val Gly Lys Asn Glu Ala Val Leu Glu Trp Asp Gln Leu Pro Val
530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
            595                 600                 605

Thr Thr Pro Lys Phe Ala Gln Gly Glu Ile Glu Ala Ile Val Val Pro
610                 615                 620

Val Cys Leu Ala Phe Leu Leu Thr Thr Leu Leu Gly Val Leu Phe Cys
625                 630                 635                 640
```

-continued

```
Phe Asn Lys Arg Asp Leu Ile Lys Lys His Ile Trp Pro Asn Val Pro
                645                 650                 655

Asp Pro Ser Lys Ser His Ile Ala Gln Trp Ser Pro His Thr Pro Pro
            660                 665                 670

Arg His Asn Phe Asn Ser Lys Asp Gln Met Tyr Ser Asp Gly Asn Phe
        675                 680                 685

Thr Asp Val Ser Val Val Glu Ile Glu Ala Asn Asp Lys Lys Pro Phe
    690                 695                 700

Pro Glu Asp Leu Lys Ser Leu Asp Leu Phe Lys Lys Glu Lys Ile Asn
705                 710                 715                 720

Thr Glu Gly His Ser Ser Gly Ile Gly Gly Ser Ser Cys Met Ser Ser
                725                 730                 735

Ser Arg Pro Ser Ile Ser Ser Ser Asp Glu Asn Glu Ser Ser Gln Asn
            740                 745                 750

Thr Ser Ser Thr Val Gln Tyr Ser Thr Val Val His Ser Gly Tyr Arg
        755                 760                 765

His Gln Val Pro Ser Val Gln Val Phe Ser Arg Ser Glu Ser Thr Gln
    770                 775                 780

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Gln Tyr Phe Lys
                805                 810                 815

Gln Asn Cys Ser Gln His Glu Ser Ser Pro Asp Ile Ser His Phe Glu
            820                 825                 830

Arg Ser Lys Gln Val Ser Ser Val Asn Glu Glu Asp Phe Val Arg Leu
        835                 840                 845

Lys Gln Gln Ile Ser Asp His Ile Ser Gln Ser Cys Gly Ser Gly Gln
    850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
                885                 890                 895

Thr Asp Glu Gly Met Pro Lys Ser Tyr Leu Pro Gln Thr Val Arg Gln
            900                 905                 910

Gly Gly Tyr Met Pro Gln
        915

<210> SEQ ID NO 4
<211> LENGTH: 862
<212> TYPE: PRT
<213> ORGANISM: Homo sapiens

<400> SEQUENCE: 4

Met Ala His Thr Phe Arg Gly Cys Ser Leu Ala Phe Met Phe Ile Ile
1               5                   10                  15

Thr Trp Leu Leu Ile Lys Ala Lys Ile Asp Ala Cys Lys Arg Gly Asp
            20                  25                  30

Val Thr Val Lys Pro Ser His Val Ile Leu Leu Gly Ser Thr Val Asn
        35                  40                  45

Ile Thr Cys Ser Leu Lys Pro Arg Gln Gly Cys Phe His Tyr Ser Arg
    50                  55                  60

Arg Asn Lys Leu Ile Leu Tyr Lys Phe Asp Arg Arg Ile Asn Phe His
65                  70                  75                  80

His Gly His Ser Leu Asn Ser Gln Val Thr Gly Leu Pro Leu Gly Thr
                85                  90                  95
```

-continued

```
Thr Leu Phe Val Cys Lys Leu Ala Cys Ile Asn Ser Asp Glu Ile Gln
            100                 105                 110

Ile Cys Gly Ala Glu Ile Phe Val Gly Val Ala Pro Glu Gln Pro Gln
        115                 120                 125

Asn Leu Ser Cys Ile Gln Lys Gly Glu Gln Gly Thr Val Ala Cys Thr
    130                 135                 140

Trp Glu Arg Gly Arg Asp Thr His Leu Tyr Thr Glu Tyr Thr Leu Gln
145                 150                 155                 160

Leu Ser Gly Pro Lys Asn Leu Thr Trp Gln Lys Gln Cys Lys Asp Ile
                165                 170                 175

Tyr Cys Asp Tyr Leu Asp Phe Gly Ile Asn Leu Thr Pro Glu Ser Pro
            180                 185                 190

Glu Ser Asn Phe Thr Ala Lys Val Thr Ala Val Asn Ser Leu Gly Ser
        195                 200                 205

Ser Ser Ser Leu Pro Ser Thr Phe Thr Phe Leu Asp Ile Val Arg Pro
    210                 215                 220

Leu Pro Pro Trp Asp Ile Arg Ile Lys Phe Gln Lys Ala Ser Val Ser
225                 230                 235                 240

Arg Cys Thr Leu Tyr Trp Arg Asp Glu Gly Leu Val Leu Leu Asn Arg
                245                 250                 255

Leu Arg Tyr Arg Pro Ser Asn Ser Arg Leu Trp Asn Met Val Asn Val
            260                 265                 270

Thr Lys Ala Lys Gly Arg His Asp Leu Leu Asp Leu Lys Pro Phe Thr
        275                 280                 285

Glu Tyr Glu Phe Gln Ile Ser Ser Lys Leu His Leu Tyr Lys Gly Ser
    290                 295                 300

Trp Ser Asp Trp Ser Glu Ser Leu Arg Ala Gln Thr Pro Glu Glu Glu
305                 310                 315                 320

Pro Thr Gly Met Leu Asp Val Trp Tyr Met Lys Arg His Ile Asp Tyr
                325                 330                 335

Ser Arg Gln Gln Ile Ser Leu Phe Trp Lys Asn Leu Ser Val Ser Glu
            340                 345                 350

Ala Arg Gly Lys Ile Leu His Tyr Gln Val Thr Leu Gln Glu Leu Thr
        355                 360                 365

Gly Gly Lys Ala Met Thr Gln Asn Ile Thr Gly His Thr Ser Trp Thr
    370                 375                 380

Thr Val Ile Pro Arg Thr Gly Asn Trp Ala Val Ala Val Ser Ala Ala
385                 390                 395                 400

Asn Ser Lys Gly Ser Ser Leu Pro Thr Arg Ile Asn Ile Met Asn Leu
                405                 410                 415

Cys Glu Ala Gly Leu Leu Ala Pro Arg Gln Val Ser Ala Asn Ser Glu
            420                 425                 430

Gly Met Asp Asn Ile Leu Val Thr Trp Gln Pro Pro Arg Lys Asp Pro
        435                 440                 445

Ser Ala Val Gln Glu Tyr Val Val Glu Trp Arg Glu Leu His Pro Gly
    450                 455                 460

Gly Asp Thr Gln Val Pro Leu Asn Trp Leu Arg Ser Arg Pro Tyr Asn
465                 470                 475                 480

Val Ser Ala Leu Ile Ser Glu Asn Ile Lys Ser Tyr Ile Cys Tyr Glu
                485                 490                 495

Ile Arg Val Tyr Ala Leu Ser Gly Asp Gln Gly Gly Cys Ser Ser Ile
            500                 505                 510
```

-continued

| | | | | | | | | | | | | |
|---|---|---|---|---|---|---|---|---|---|---|---|---|
| Leu | Gly | Asn | Ser | Lys | His | Lys | Ala | Pro | Leu | Ser | Gly | Pro | His | Ile | Asn |
| | | 515 | | | | 520 | | | | | 525 | | | | |
| Ala | Ile | Thr | Glu | Glu | Lys | Gly | Ser | Ile | Leu | Ile | Ser | Trp | Asn | Ser | Ile |
| | 530 | | | | | 535 | | | | | 540 | | | | |
| Pro | Val | Gln | Glu | Gln | Met | Gly | Cys | Leu | Leu | His | Tyr | Arg | Ile | Tyr | Trp |
| 545 | | | | | 550 | | | | | 555 | | | | | 560 |
| Lys | Glu | Arg | Asp | Ser | Asn | Ser | Gln | Pro | Gln | Leu | Cys | Glu | Ile | Pro | Tyr |
| | | | 565 | | | | | 570 | | | | | 575 | | |
| Arg | Val | Ser | Gln | Asn | Ser | His | Pro | Ile | Asn | Ser | Leu | Gln | Pro | Arg | Val |
| | | | 580 | | | | | 585 | | | | 590 | | | |
| Thr | Tyr | Val | Leu | Trp | Met | Thr | Ala | Leu | Thr | Ala | Ala | Gly | Glu | Ser | Ser |
| | | 595 | | | | | 600 | | | | | 605 | | | |
| His | Gly | Asn | Glu | Arg | Glu | Phe | Cys | Leu | Gln | Gly | Lys | Ala | Asn | Trp | Met |
| | 610 | | | | | 615 | | | | | 620 | | | | |
| Ala | Phe | Val | Ala | Pro | Ser | Ile | Cys | Ile | Ala | Ile | Met | Val | Gly | Ile |
| 625 | | | | | 630 | | | | | 635 | | | | 640 |
| Phe | Ser | Thr | His | Tyr | Phe | Gln | Gln | Lys | Val | Phe | Val | Leu | Leu | Ala | Ala |
| | | | | 645 | | | | | 650 | | | | | 655 | |
| Leu | Arg | Pro | Gln | Trp | Cys | Ser | Arg | Glu | Ile | Pro | Asp | Pro | Ala | Asn | Ser |
| | | | 660 | | | | | 665 | | | | | 670 | | |
| Thr | Cys | Ala | Lys | Lys | Tyr | Pro | Ile | Ala | Glu | Glu | Lys | Thr | Gln | Leu | Pro |
| | | | 675 | | | | | 680 | | | | | 685 | | |
| Leu | Asp | Arg | Leu | Leu | Ile | Asp | Trp | Pro | Thr | Pro | Glu | Asp | Pro | Glu | Pro |
| | 690 | | | | | 695 | | | | | 700 | | | | |
| Leu | Val | Ile | Ser | Glu | Val | Leu | His | Gln | Val | Thr | Pro | Val | Phe | Arg | His |
| 705 | | | | | 710 | | | | | 715 | | | | | 720 |
| Pro | Pro | Cys | Ser | Asn | Trp | Pro | Gln | Arg | Glu | Lys | Gly | Ile | Gln | Gly | His |
| | | | | 725 | | | | | 730 | | | | | 735 | |
| Gln | Ala | Ser | Glu | Lys | Asp | Met | Met | His | Ser | Ala | Ser | Ser | Pro | Pro | Pro |
| | | | 740 | | | | | 745 | | | | | 750 | | |
| Pro | Arg | Ala | Leu | Gln | Ala | Glu | Ser | Arg | Gln | Leu | Val | Asp | Leu | Tyr | Lys |
| | | 755 | | | | | 760 | | | | | 765 | | | |
| Val | Leu | Glu | Ser | Arg | Gly | Ser | Asp | Pro | Lys | Pro | Glu | Asn | Pro | Ala | Cys |
| | 770 | | | | | 775 | | | | | 780 | | | | |
| Pro | Trp | Thr | Val | Leu | Pro | Ala | Gly | Asp | Leu | Pro | Thr | His | Asp | Gly | Tyr |
| 785 | | | | | 790 | | | | | 795 | | | | | 800 |
| Leu | Pro | Ser | Asn | Ile | Asp | Asp | Leu | Pro | Ser | His | Glu | Ala | Pro | Leu | Ala |
| | | | | 805 | | | | | 810 | | | | | 815 | |
| Asp | Ser | Leu | Glu | Glu | Leu | Glu | Pro | Gln | His | Ile | Ser | Leu | Ser | Val | Phe |
| | | | 820 | | | | | 825 | | | | | 830 | | |
| Pro | Ser | Ser | Ser | Leu | His | Pro | Leu | Thr | Phe | Ser | Cys | Gly | Asp | Lys | Leu |
| | | 835 | | | | | 840 | | | | | 845 | | | |
| Thr | Leu | Asp | Gln | Leu | Lys | Met | Arg | Cys | Asp | Ser | Leu | Met | Leu |
| 850 | | | | | 855 | | | | | 860 | | | |

IL-23 RECEPTOR BINDING COMPOSITIONS

This filing claims benefit of U.S. Provisional Patent Application No. 60/203,426, filed May 10, 2000 which is incorporated herein by reference in its entirety.

FIELD OF THE INVENTION

The present invention relates to compositions and methods for affecting mammalian physiology, including immune system function. In particular, it provides methods to regulate development and/or the immune system. Diagnostic and therapeutic uses of these materials are also disclosed.

BACKGROUND OF THE INVENTION

Recombinant DNA technology refers generally to techniques of integrating genetic information from a donor source into vectors for subsequent processing, such as through introduction into a host, whereby the transferred genetic information is copied and/or expressed in the new environment. Commonly, the genetic information exists in the form of complementary DNA (cDNA) derived from messenger RNA (mRNA) coding for a desired protein product. The carrier is frequently a plasmid having the capacity to incorporate cDNA for later replication in a host and, in some cases, actually to control expression of the cDNA and thereby direct synthesis of the encoded product in the host. See, e.g., Sambrook, et al. (1989) Molecular Cloning: A Laboratory Manual, (2d ed.) vols. 1–3, CSH Press, N.Y.

For some time, it has been known that the mammalian immune response is based on a series of complex cellular interactions, called the "immune network". Recent research has provided new insights into the inner workings of this network. While it remains clear that much of the immune response does, in fact, revolve around the network-like interactions of lymphocytes, macrophages, granulocytes, and other cells, immunologists now generally hold the opinion that soluble proteins, known as lymphokines, cytokines, or monokines, play critical roles in controlling these cellular interactions. Thus, there is considerable interest in the isolation, characterization, and mechanisms of action of cell modulatory factors, an understanding of which will lead to significant advancements in the diagnosis and therapy of numerous medical abnormalities, e.g., immune system disorders.

Lymphokines apparently mediate cellular activities in a variety of ways. See, e.g., Paul (ed. 1996) Fundamental Immunology 3d ed., Raven Press, New York; and Thomson (ed. 1994) The Cytokine Handbook 2d ed., Academic Press, San Diego. They have been shown to support the proliferation, growth, and/or differentiation of pluripotential hematopoietic stem cells into vast numbers of progenitors comprising diverse cellular lineages which make up a complex immune system. Proper and balanced interactions between the cellular components are necessary for a healthy immune response. The different cellular lineages often respond in a different manner when lymphokines are administered in conjunction with other agents.

Cell lineages especially important to the immune response include two classes of lymphocytes: B-cells, which can produce and secrete immunoglobulins (proteins with the capability of recognizing and binding to foreign matter to effect its removal), and T-cells of various subsets that secrete lymphokines and induce or suppress the B-cells and various other cells (including other T-cells) making up the immune network. These lymphocytes interact with many other cell types.

Research to better understand and treat various immune disorders has been hampered by the general inability to maintain cells of the immune system in vitro. Immunologists have discovered that culturing many of these cells can be accomplished through the use of T-cell and other cell supernatants, which contain various growth factors, including many of the lymphokines.

Various growth and regulatory factors exist which modulate morphogenetic development. Many receptors for cytokines are known. Often, there are at least two critical subunits in the functional receptor. See, e.g., Heinrich, et al. (1998) Biochem. J. 334:297–314; Gonda and D'Andrea (1997) Blood 89:355–369; Presky, et al. (1996) Proc. Nat'l Acad. Sci. USA 93:14002–14007; Drachman and Kaushansky (1995) Curr. Opin. Hematol. 2:22–28; Theze (1994) Eur. Cytokine Netw. 5:353–368; and Lemmon and Schlessinger (1994) Trends Biochem. Sci. 19:459–463.

From the foregoing, it is evident that the discovery and development of new soluble proteins and their receptors, including ones similar to lymphokines, should contribute to new therapies for a wide range of degenerative or abnormal conditions which directly or indirectly involve development, differentiation, or function, e.g., of the immune system and/or hematopoietic cells. In particular, the discovery and understanding of novel receptors for lymphokine-like molecules which enhance or potentiate the beneficial activities of other lymphokines would be highly advantageous. The present invention provides new receptors for ligands exhibiting similarity to cytokine like compositions and related compounds, and methods for their use.

SUMMARY OF THE INVENTION

The present invention is directed to novel receptors related to cytokine receptors, e.g., primate, cytokine receptor-like molecular structures, designated DNAX Cytokine Receptor Subunits (DCRS), and their biological activities. In particular, it provides description of one subunit, designated DCRS5. It includes nucleic acids coding for the polypeptides themselves and methods for their production and use. The nucleic acids of the invention are characterized, in part, by their homology to cloned complementary DNA (cDNA) sequences enclosed herein. Additionally, the invention provides matching of the p40/IL-B30 ligand with receptor subunits DCRS5 and IL-12Rβ1, which pairing provides insight into indications for use of the agonists and antagonists based upon reagents directed thereto.

The present invention provides a substantially pure or recombinant polypeptide comprising at least ten contiguous amino acids of the intracellular portion of SEQ ID NO: 2. In certain embodiments, the polypeptide: comprises at least 25 contiguous amino acids of the intracellular portion of SEQ ID NO: 2; is recombinant, comprising the intracellular portion of SEQ ID NO: 2; further comprises at least ten contiguous amino acids of the non-intracellular portion of SEQ ID NO: 2; comprises at least 25 amino acids of the extracellular portion of SEQ ID NO: 2; comprises the mature SEQ ID NO: 2; or is a substantially pure natural polypeptide. In others, the recombinant polypeptide: consists of the mature sequence of SEQ ID NO:2; is an unglycosylated polypeptide; is from a human; comprises at least 40 contiguous amino acids of SEQ ID NO: 2; exhibits at least three nonoverlapping segments of at least fifteen contiguous amino acids of SEQ ID NO: 2; is a natural polymorphic variant of SEQ ID NO: 2; has a length at least about 30 amino acids; exhibits at least two non-overlapping epitopes which are specific for a primate DCRS5; has a molecular weight of at least 30 kD with natural glycosylation; is a synthetic polypeptide; is in a sterile form; is in an aqueous or buffered solution; is attached to a solid substrate; is conjugated to another chemical moiety; or is physically associated with an IL-12Rβ1 polypeptide.

Other embodiments of the invention provide: a substantially pure or recombinant polypeptide comprising at least two distinct nonoverlapping segments of at least six contiguous amino acids of the intracellular portion of SEQ ID NO:2; a substantially pure or recombinant polypeptide comprising at least twelve contiguous amino acids of the intracellular portion of SEQ ID NO: 2; or a substantially pure natural sequence polypeptide comprising mature SEQ ID NO: 2. In particular forms, the polypeptide comprising at least two distinct nonoverlapping segments of at least six contiguous amino acids of the intracellular portion of SEQ ID NO: 2 will be where: the distinct nonoverlapping segments: include one of at least twelve amino acids; include one of at least seven amino acids and a second of at least nine amino acids; include a third distinct segment of at least six amino acids; or comprise one of R355-L373, P378-L405, V407-D426, K428-D439, P441-V452, I454-G460, I465-T587, or N592–606; or the polypeptide further comprises at least two distinct nonoverlapping segments of at least six contiguous amino acids of the extracellular portion of SEQ ID NO: 2. Alternatively, the polypeptide comprising at least twelve contiguous amino acids of the intracellular portion of SEQ ID NO: 2 will be one where: the at least twelve contiguous amino acid segment comprises one of R355-L373, P378-L405, V407-D426, K428-D439, P441-V452, I454-G460, I465-T587, or N592–606; or the polypeptide further comprises at least two distinct nonoverlapping segments of at least six contiguous amino acids of the extracellular portion of SEQ ID NO: 2. Or, the pure natural sequence polypeptide comprising mature SEQ ID NO: 2 may further comprising a purification or detection epitope. Such polypeptides may: consist of the mature sequence of SEQ ID NO:2; be an unglycosylated polypeptide; be from a human; comprise at least 40 contiguous amino acids of SEQ ID NO: 2; exhibit at least three nonoverlapping segments of at least fifteen contiguous amino acids of SEQ ID NO: 2; be a natural polymorphic variant of SEQ ID NO: 2; have a length at least about 30 amino acids; exhibit at least two non-overlapping epitopes which are specific for a primate DCRS5 (SEQ ID NO:2); have a molecular weight of at least 30 kD with natural glycosylation; be a synthetic polypeptide; be in a sterile form; be in an aqueous or buffered solution; be attached to a solid substrate; be conjugated to another chemical moiety; or be physically associated with an IL-12Rβ1 polypeptide.

Various other compositions are provided, e.g., comprising: a substantially pure polypeptide combined with the IL-12Rβ1 protein; or such a polypeptide in a carrier, wherein the carrier is: an aqueous compound, including water, saline, and/or buffer; and/or formulated for oral, rectal, nasal, topical, or parenteral administration.

Kits are provided comprising such a polypeptide and: a compartment comprising the polypeptide; a compartment comprising an IL-12Rβ1 polypeptide; a compartment comprising a p40, IL-B30, or p40/IL-B30 polypeptide; or instructions for use or disposal of reagents in the kit.

Antibodies and other binding compounds are provided, e.g., comprising an antigen binding site from an antibody, which specifically binds to the intracellular portion of the DCRS5, wherein: the binding compound is in a container; the polypeptide is from a human; the binding compound is an Fv, Fab, or Fab2 fragment; the binding compound is conjugated to another chemical moiety; or the antibody: is raised against a peptide sequence of a mature polypeptide of Table 1; is raised against a mature DCRS5; is raised to a purified human DCRS5; is immunoselected; is a polyclonal antibody; binds to a denatured DCRS5; exhibits a Kd to antigen of at least 30 μm; is attached to a solid substrate, including a bead or plastic membrane; is in a sterile composition; or is detectably labeled, including a radioactive or fluorescent label. Kits are also provided comprising the binding compound and: a compartment comprising the binding compound; a compartment comprising: a p40 polypeptide; an IL-B30 polypeptide; a DCRS5 polypeptide; and/or an IL-12Rβ1 polypeptide; a compartment comprising an antibody which binds selectively to: a p40 polypeptide; an IL-B30 polypeptide; a DCRS5 polypeptide; and/or an IL-12Rβ1 polypeptide; or instructions for use or disposal of reagents in the kit.

Also provided are methods, e.g., of producing an antigen:antibody complex, comprising contacting under appropriate conditions a primate DCRS5 polypeptide with an antibody, thereby allowing the complex to form. Such method may be where: the complex is purified from other cytokine receptors; the complex is purified from other antibody; the contacting is with a sample comprising an interferon; the contacting allows quantitative detection of the antigen; the contacting is with a sample comprising the antibody; or the contacting allows quantitative detection of the antibody. Other compositions are provided, e.g., composition comprising: a sterile binding compound, or the binding compound and a carrier, wherein the carrier is: an aqueous compound, including water, saline, and/or buffer; and/or formulated for oral, rectal, nasal, topical, or parenteral administration.

The invention also provides an isolated or recombinant nucleic acid encoding the DCRS5 (SEQ ID NO:2) polypeptide, wherein the: DCRS5 is from a human; or the nucleic acid: encodes an antigenic peptide sequence of SEQ ID NO:2; encodes a plurality of antigenic peptide sequences of SEQ ID NO:2; exhibits identity over at least thirteen nucleotides to a natural cDNA encoding the segment; is an expression vector; further comprises an origin of replication; is from a natural source; comprises a detectable label; comprises synthetic nucleotide sequence; is less than 6 kb, preferably less than 3 kb; is from a primate; comprises a natural full length coding sequence; is a hybridization probe for a gene encoding the DCRS5 (SEQ ID NO:2); or is a PCR primer, PCR product, or mutagenesis primer. Cells comprising the recombinant nucleic acid are provided, including where the cell is: a prokaryotic cell; a eukaryotic cell; a bacterial cell; a yeast cell; an insect cell; a mammalian cell; a mouse cell; a primate cell; or a human cell.

Kit embodiments include those comprising the nucleic acid and: a compartment comprising the nucleic acid; a compartment comprising a nucleic acid encoding: a p40 polypeptide; an IL-B30 polypeptide; a DCRS5 polypeptide; and/or an IL-12Rβ1 polypeptide; a compartment comprising: a p40 polypeptide; an IL-B30 polypeptide; a DCRS5 polypeptide; and/or an IL-12Rβ1 polypeptide; a compartment comprising an antibody which selectively binds to: a p40 polypeptide; an IL-B30 polypeptide; a DCRS5 polypeptide; and/or an IL-12Rβ1 polypeptide; or instructions for use or disposal of reagents in the kit.

Other nucleic acid embodiments include those which: hybridize under wash conditions of 30 minutes at 30° C. and less than 2M salt to the portion of SEQ ID NO:1 encoding the intracellular portion; or exhibit identity over a stretch of at least about 30 nucleotides to the intracellular portion of a primate DCRS5. Preferably, such nucleic acid will be one wherein: the wash conditions are at 45° C. and/or 500 mM salt; or 55° C. and/or 150 mM salt; or the stretch is at least 55 or 75 nucleotides.

Therapeutic uses include methods of modulating physiology or development of a cell comprising contacting the cell with: an antagonist of p40/IL-B30 which is a complex comprising: the extracellular portion of a primate DCRS5 and/or the extracellular portion of a primate IL-12Rβ1; an antagonist of p40/IL-B30 which is an antibody which binds a complex comprising: primate DCRS5 and/or primate IL-12Rβ1; an antagonist of p40/IL-B30 which is an antibody which binds to DCRS5; an antagonist of p40/IL-B30 which is an antibody to IL-12Rβ1; an antagonist of p40/IL-B30 which is an antisense nucleic acid to DCRS5 or IL-12Rβ1; or an agonist of p40/IL-B30 which is an antibody which binds a complex comprising primate DCRS5 and/or primate IL-12Rβ1. In one type of method, the contacting is with an antagonist, and the contacting is in combination with an antagonist to IL-12, IL-18, TNF, and/or IFNγ; or the cell is from a host which: exhibits signs or symptoms of a chronic TH1 mediated disease; exhibits symptoms or signs of multiple sclerosis, rheumatoid arthritis, osteoarthritis, inflammatory bowel disease, diabetes, psoriasis, or sepsis; or receives an allogeneic transplant. Conversely, the method may be contacting with an agonist, and: the contacting is in combination with IL-12, IL-18, TNF, or IFNγ; or the cell is from a host which: exhibits signs or symptoms of a chronic Th2 response; suffers from a tumor, viral, or fungal growth; receives a vaccine; or suffers from an allergic response.

DETAILED DESCRIPTION OF THE PREFERRED EMBODIMENTS

Outline

I. General
II. Activities
III. Nucleic acids
   A. encoding fragments, sequence, probes
   B. mutations, chimeras, fusions
   C. making nucleic acids
   D. vectors, cells comprising
IV. Proteins, Peptides
   A. fragments, sequence, immunogens, antigens
   B. muteins
   C. agonists/antagonists, functional equivalents
   D. making proteins
V. Making nucleic acids, proteins
   A. synthetic
   B. recombinant
   C. natural sources
VI. Antibodies
   A. polyclonals
   B. monoclonal
   C. fragments; Kd
   D. anti-idiotypic antibodies
   E. hybridoma cell lines
VII. Kits, Diagnosis, and Quantitation
   A. ELISA
   B. assay mRNA encoding
   C. qualitative/quantitative
   D. kits
VIII. Therapeutic compositions, methods
   A. combination compositions
   B. unit dose
   C. administration
IX. Screening I. General The present invention provides the amino acid sequence and DNA sequence of mammalian, herein primate, cytokine receptor-like subunit molecules, this one designated DNAX Cytokine Receptor Subunit 5 (DCRS5) having particular defined properties, both structural and biological. Various cDNAs encoding these molecules were obtained from primate, e.g., human, cDNA sequence libraries. Other primate or other mammalian counterparts would also be desired.

Additionally, the invention provides matching of the p40/IL-B30 ligand with receptor subunits DCRS5 and IL-12Rβ1, which pairing provides insight into indications for use of the agonists and antgonists based upon reagents directed thereto.

Some of the standard methods applicable are described or referenced, e.g., in Maniatis, et al. (1982) Molecular Cloning, A Laboratory Manual, Cold Spring Harbor Laboratory, Cold Spring Harbor Press; Sambrook, et al. (1989) Molecular Cloning: A Laboratory Manual, (2d ed.), vols. 1 3, CSH Press, NY; Ausubel, et al., Biology, Greene Publishing Associates, Brooklyn, N.Y.; or Ausubel, et al. (1987 and periodic supplements) Current Protocols in Molecular Biology, Greene/Wiley, New York; each of which is incorporated herein by reference.

Nucleotide (SEQ ID NO:1) and corresponding amino acid sequence (SEQ ID NO:2) of a primate, e.g., human, DCRS5 coding segment is shown in Table 1. The predicted signal sequence is indicated, but may depend on cell type, or may be a few residues in either direction. Potential N glycosylation sites are at Asparagine residues 6, 24, 58, 118, 157, 209, and 250. Disulfide linkages are likely to be found between cysteine residues at positions 29 and 78; and a conserved C_CXW motif is found at positions 110/121/123. The tryptophan at 219; and the WxxWS motif from 281–285 are notable. The segment from about 1–101 is an Ig domain; from about 102–195 is a cytokine binding domain 1; from about 196–297 is a cytokine binding domain 2; from about 298–330 is a linker; from about 329–354 is a transmembrane segment; and from about 356–606 is an intracellular domain. Intracellular features include putative SH2 binding sites at Y374-I377, Y461-Q464, and Y588-Q591; and potentially important tyrosine residues at 406, 427, 440, and 453. These sites and boundaries are notable.

The ORF contains a putative signal sequence which is predicted to be cleaved at . . . CHG/GIT . . . as shown above. A predicted extracellular domain of 328 amino acids is followed by a putative transmembrane segment, and finally a cytoplasmic domain of about 252 amino acids. The ligand-binding functions are predicted to reside in the extracellular domain.

The reverse translation nucleic acid sequence is provided in Table 2.

TABLE 1

Alignment of various cytokine receptor subunits. Human DCRS5 is SEQ ID NO:2. Human IL-6 receptor protein gp130 is SEQ ID NO: 3 (GenBank M57230); human IL-12 receptor beta2 subunit is SEQ ID NO: 4 (GenBank U64198).

```
huIL-12R 2     1   MAHTFRGCSLAFMFIITWLLIKAKIDACKRGDVTVKPSHVILLGSTVN     48
hugp130        1   MLTLQTWVVQALFIFLTTESTGELLDPCG---YISPESPVVQLHSNFT     45
huDCRS5        1   MNHVTIQWDAVIALYILFSWCHGGITNINCS-GHIWVEPATIFKMGMNIS   49
                          *       .    *            .  * . . . .

huIL-12R 2    49   ITCSLKPRQGCFHYSRRNKLILYKFDRRINFHHGHSLNSQVTGLPLG---    95
hugp130       46   AVCVLKEKCMDYFHVNANYIVWKTNHFTIPKEQYTIINRTASSVTFTDIA    95
huDCRS5       50   IYCQAAIKN--CQP---RKLHFYKNGIKER-FQITRINKTTARLWYKNFL    93
                     *     .      .       .       .  .*   .    .

huIL-12R 2    96   --TTLFVCKLACINSD-EIQICGAEIFVGVAPEQPQNLSCIQKGEQGTVA   142
hugp130       96   SLNIQLTCNILTFGQL-EQNVYGITIISGLPPEKPKNLSCIVN-EGKKMR   143
hnDCRS5       94   EPHASMYCTAECPKHFQETLICGKDISSGYPPDIPDEVTCVIYEYSGNMT   143
                       *  .     *  .  *  *  *  *.  * .    . . .*.   .

huIL-12R 2   143   CTWERGRDTHLYTEYTLQLSGPKNLTWQKQCKDIYCDYLDFGINLTPESP   192
hugp130      144   CEWDGGRETHLETNFTLKS--EWATHKFADCKAKRDTPTSCTVDYS-TVY   190
huDCRS5      144   CTWNARKLTYIDTKYVVHVKSLETEEEQQYLTSSYINISTDSLQGG----   189
                   * *   .  * . * . . .

huIL-12R 2   193   ESNFTAKVTAVNSLGSSSSLPSTFTFLDIVRPLPPWDIRIKFQKASVSRC   242
hngp130      191   FVNIEVWVEAENALGKVTSDHINFDPVYKVKPNPPHNLSVINSEELSSIL   240
huDCRS5      190   -KKYLVWVQAANALGMEESKQLQIHLDDIVIPSAAVISRAETINATVPKT   238
                     *  * *.**       *              *   * huIL-12R 2   243   TLYWRD----EGLVLLNRLRYRPSNSRLNNMVN---VTKAKGRHDLLDLK   285
hugp130      241   KLTWTNPSIKSVIILKYNIQYRTKDASTWSQIPPEDTASTRSSFTVQDLK   290
huDCRS5      239   IIYWDS--QTTIEKVSCEMRYKATTNQTWNVKEFD-TNFTYVQQSEFYLE   285
                    . *       .    . .*.    *           *           * huIL-12R 2   286   PFTEYEFQISSKLHLYKGSWSDWSESLRAQTPEEEPTGMLDVWYMKRHID   335
hugp130      291   PFTEYVFRIRCMKEDGKGYWSDWSEEASGITYEDRPSKAPSFWYKIDPSH   340
huDCRS5      286   PNIKYVFQVRCQ-ETGKRYWQPWSSPFFHKTPETVP--------------   320
                   *  *  *...   *  *              * * huIL-12R 2   336   YS-RQQISLFWKNLSVSEARGKILHYQVTLQELTGGKAMTQNITGHTSWT   384
hugp130      341   TQGYRTVQLVWKTLPPFEANGKILDYEVT---LTRWKSHLQNYTVNATKL   387
huDCRS5      321   -----QVTSKAFQHDTWNSGLTVASISTG------HLTSDN--RGDIGLL   357
                             .        . .            . .

huIL-12R 2   385   TVIPRTGNWAVAVSAANSKGSSLPTRINIMNLCEAGLLAPRQVSANSEGM   434
hugp130      386   TVNLTNDRYLATLTVRNLVGKSDAAVLTIP-ACDFQATRPVMDLKAFPKD   436
huDCRS5      358   LGMIVFAVMLSILSLIGIFNRSFRTGIKRR--------------------   387
                    ..  .  *  ..

huIL-12R 2   435   DNILVTWQPPRKDPSAVQEYVVEWRELHPG-GDTQVPLNWLRSRPYNVSA   483
hugp130      437   NMLWVEWTTPRE---SVKKYILEWCVLS---DKAPCITDWQQEDGTVHRT   480
huDCRS5      388   ----------------ILLLIPKWLYEDIPNMKNSNVVKMLQEN----SE   417
                                     .    .  *               .

huIL-12R 2   484   LISENIKSYICYEIRVYALSGDQ-GGCSSILGNSKHKAPLSGPHINAITE   532
hugp130      481   YLRGNLAESKCYLITVTPVYADGPGSPESIKAYLKQAPPSKGPTVRTKKV   530
huDCRS5      418   LMNNNSSE--------QVLYVDP-----MITEIKEIFIPEHKPTDYKKE-   453
                   . *                *  *       *    *   * huIL-12R 2   533   EKGSILISWNSIPVQEQMGCLLHYRIYWKERDSNSQPQLCEIPYRVSQNS   582
hugp130      531   GKNEAVLEWDQLPVDVQNGFIRNYTIFYRTIIGN----ETAVNVDSSHTE   576
huDCRS5      454   --NTGPLETRDYP---QNSLFDNTTVVYIPDLNTG------YKPQISN--   490
                     .           *  *         .   .                * * huIL-12R 2   583   HPINSLQPRVTYVLWMTALTAAGESSHGNEREFCLQGKAN-WMAFVAPSI   631
hugp130      577   YTLSSLTSDTLYMVRMAAYTDEG-GKDGPEFTFTTPKFAQGEIEAIVVPV   625
huDCRS5      491   ------------------FLPEG---------------------------   495
                                          * huIL-12R 2   632   CIAIIMVGIFSTHYFQQKVFVLLAALRP-----------QWCSREIPDPA   670
hugp130      626   CLAFLLTTLLGVLFCFNKRDLIKKHIWPNVPDPSKSHIAQWSPHTPPRHN   675
huDCRS5      496   -----------SHLSNNN-EITSTLTKP--------------PVDSLDSG   519
                              .  .    . * huIL-12R 2   671   NSTCAKKYPIAEEKTQLPLDRLLID-WPTPEDPEPLVIS--EVLHQVTPV   717
hugp130      676   FNSKDQMYSDGNFTDVSVVEIEANDKKPFPEDLKSLDLFKKEKINTEGHS   725
huDCRS5      520   NNPRLQKHPN-FAFSVSSVNSLSNT--------------I---FLGELSLI   552
                               .                          .
```

TABLE 1-continued

Alignment of various cytokine receptor subunits. Human DCRS5 is
SEQ ID NO:2. Human IL-6 receptor protein gp130 is SEQ ID NO: 3
(GenBank M57230); human IL-12 receptor beta2 subunit is SEQ ID
NO: 4 (GenBank U64198).

```
huIL-12R 2   718  FRHPPCSNWPQREKGIQGHQASEKDMMHSASSPPPPPRALQESRQLVDLY      767
hugp130      726  SGIGGSSCMSSSRPSISSSDENESSQNTSSTVQYSTVVHSGYRHQVPSVQ      775
huDCRS5      553  LNQGECS---S--PDIQNSVEEETTMLLENDSP-----------------      580
                          .*      *      * huIL-12R 2   768  KVLESRGSDPKPENPACPWTVLPAGDLPTHDGYLPSN---IDDLPSHEAP      814
hugp130      776  VFSRSESTQPLLDSEERPEDLQLVDHVDGGDGILPRQQYFKQNCSQHESS      825
huDCRS5      581  --SETIPEQTLLPDEFVSCLGIVNEELPSINTYFPQN---ILESHFNR--      623
                      .                           .    *  .         .

huIL-12R 2   815  LADSLEELEPQHISLS-----VFPSSSLHPLTFSCG--------------      845
hugp130      826  PDISHFERSKQVSSVNEEDFVRLKQQISDHISQSCGSGQMKMFQEVSAAD      875
huDCRS5      624  --ISLLEK                                                629
                      *  * huIL-12R 2   846  ----------DKLTLDQLKMRCDSLML                             862
hugp130      876  AFGPGTEGQVERFETVGMEAATDEGMPKSYLPQTVRQGGYMPQ             918
huDCRS5      630                                                          629
```

The closest relatives of the extracellular domain of "IL-30R" are the IL-6 signal transducer gp130 and IL-12Rβ2. Somewhat less close relatives are GCSF receptor, leptin receptor, leukemia inhibitory factor receptor, and CNTF receptor. Thus "IL-30R" is a member of the class I branch of the cytokine receptor superfamily and is closely related to the IL-6R/IL-12R family.

Table 1 shows comparison of the available sequences of primate receptor subunits with the primate, e.g., human DCRS5 (IL-30R). The DCRS5 shows similarity to the IL-6 receptor subunit gp130 (e.g., IL-6R subunit) and the IL-12Rβ2 subunit. The DCRS5 exhibits structural features of a beta subunit, but the actual sequence of protein interactions and signaling remains unresolved.

As used herein, the term DCRS5 shall be used to describe a protein comprising the amino acid sequence shown in SEQ ID NO:2. In many cases, a substantial fragment thereof will be functionally or structurally equivalent, including, e.g., additional extracellular segments. The invention also includes a protein variation of the respective DCRS5 allele whose sequence is provided, e.g., a mutein or other construct. Typically, such variants will exhibit less than about 10% sequence differences with the target region, and thus will often have between 1- and 11-fold substitutions, e.g., 2-, 3-, 5, 7-fold, and others. It also encompasses allelic and other variants, e.g., natural polymorphisms, of the protein described. Typically, it will bind to its corresponding biological ligand, perhaps in a dimerized state with an alpha receptor subunit, with high affinity, e.g., at least about 100 nM, usually better than about 30 nM, preferably better than about 10 nM, and more preferably at better than about 3 nM. The term shall also be used herein to refer to related naturally occurring forms, e.g., alleles, polymorphic variants, and metabolic variants of the mammalian protein. Preferred forms of the receptor complexes will bind the appropriate ligand with an affinity and selectivity appropriate for a ligand-receptor interaction.

This invention also encompasses combinations of proteins or peptides having substantial amino acid sequence identity with the amino acid sequence SEQ ID NO:2. It will include sequence variants with relatively few substitutions, e.g., preferably fewer than about 3–5.

A substantial polypeptide "fragment", or "segment", is a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids. Sequences of segments of different proteins can be compared to one another over appropriate length stretches. In many situations, fragments may exhibit functional properties of the intact subunits, e.g., the extracellular domain of the transmembrane receptor may retain the ligand binding features, and may be used to prepare a soluble receptor-like complex.

Amino acid sequence homology, or sequence identity, is determined by optimizing residue matches. In some comparisons, gaps may be introduces, as required. See, e.g., Needleham, et al., (1970) J. Mol. Biol. 48:443–453; Sankoff, et al., (1983) chapter one in Time Warps, String Edits, and Macromolecules: The Theory and Practice of Sequence Comparison, Addison-Wesley, Reading, Mass.; and software packages from IntelliGenetics, Mountain View, Calif.; and the University of Wisconsin Genetics Computer Group (GCG), Madison, Wis.; each of which is incorporated herein by reference. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences are intended to include natural allelic and interspecies variations in the cytokine sequence. Typical homologous proteins or peptides will have from 50 100% homology (if gaps can be introduced), to 60 100% homology (if conservative substitutions are included) with an amino acid sequence segment of SEQ ID NO:2. Homology measures will be at least about 70%, generally at least 76%, more generally at least 81%, often at least 85%, more often at least 88%, typically at least 90%, more typically at least 92%, usually at least 94%, more usually at least 95%, preferably at least 96%, and more preferably at least 97%, and in particularly preferred embodiments, at least 98% or more. The degree of homology will vary with the length of the compared segments. Homologous proteins or peptides, such as the allelic variants, will share most biological activities with the embodiments SEQ ID NO:2, particularly the intracellular portion.

As used herein, the term "biological activity" is used to describe, without limitation, effects on signaling, inflammatory responses, innate immunity, and/or morphogenic development by cytokine-like ligands. For example, these receptors should mediate phosphatase or phosphorylase activities, which activities are easily measured by standard procedures. See, e.g., Hardie, et al. (eds. 1995) The Protein Kinase FactBook vols. I and II, Academic Press, San Diego, Calif.; Hanks, et al. (1991) Meth. Enzymol. 200:38–62; Hunter, et al. (1992) Cell 70:375–388; Lewin (1990) Cell 61:743–752; Pines, et al. (1991) Cold Spring Harbor Symp. Quant. Biol. 56:449–463; and Parker, et al. (1993) Nature 363:736–738. The receptors, or portions thereof, may be useful as phosphate labeling enzymes to label general or specific substrates. The subunits may also be functional immunogens to elicit recognizing antibodies, or antigens capable of binding antibodies.

The terms ligand, agonist, antagonist, and analog of, e.g., a DCRS5 petition features of ligand-receptor interactions, e.g., where the receptor is a natural receptor or an antibody. The cellular responses likely are typically mediated through receptor tyrosine kinase pathways.

Also, a ligand is a molecule which serves either as a natural ligand to which said receptor, or an analog thereof, binds, or a molecule which is a functional analog of the natural ligand. The functional analog may be a ligand with structural modifications, or may be a wholly unrelated molecule which has a molecular shape which interacts with the appropriate ligand binding determinants. The ligands may serve as agonists or antagonists, see, e.g., Goodman, et al. (eds. 1990) Goodman & Gilman's: The Pharmacological Bases of Therapeutics, Pergamon Press, New York.

Rational drug design may also be based upon structural studies of the molecular shapes of a receptor or antibody and other effectors or ligands. See, e.g., Herz, et al. (1997) J. Recept. Signal Transduct. Res. 17:671–776; and Chaiken, et al. (1996) Trends Biotechnol. 14:369–375. Effectors may be other proteins which mediate other functions in response to ligand binding, or other proteins which normally interact with the receptor. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) Protein Crystallography, Academic Press, New York, which is hereby incorporated herein by reference.

II. Activities

The cytokine receptor-like proteins will have a number of different biological activities, e.g., intracellular signaling, e.g., via STAT4, modulating cell proliferation, or in phosphate metabolism, being added to or removed from specific substrates, typically proteins. Such will generally result in modulation of an inflammatory function, other innate immunity response, or a morphological effect. The subunit will probably have a specific low affinity binding to the ligand.

The DCRS5 (SEQ ID NOs:1 or 2) has the characteristic motifs of a receptor signaling through the JAK pathway. See, e.g., Ihle, et al. (1997) Stem Cells 15(suppl. 1):105–111; Silvennoinen, et al. (1997) APMIS 105:497–509; Levy (1997) Cytokine Growth Factor Review 8:81–90; Winston and Hunter (1996) Current Biol. 6:668–671; Barrett (1996) Baillieres Clin. Gastroenterol. 10:1–15; and Briscoe, et al. (1996) Philos. Trans. R. Soc. Lond. B. Biol. Sci. 351:167–171. Of particular interest are the SH2 binding motifs described above.

The biological activities of the cytokine receptor subunits will be related to addition or removal of phosphate moieties to substrates, typically in a specific manner, but occasionally in a non specific manner. Substrates may be identified, or conditions for enzymatic activity may be assayed by standard methods, e.g., as described in Hardie, et al. (eds. 1995) The Protein Kinase FactBook vols. I and II, Academic Press, San Diego, Calif.; Hanks, et al. (1991) Meth. Enzymol. 200:38–62; Hunter, et al. (1992) Cell 70:375–388; Lewin (1990) Cell 61:743–752;

Pines, et al. (1991) Cold Spring Harbor Symp. Quant. Biol. 56:449–463; and Parker, et al. (1993) Nature 363:736–738.

The receptor subunits may combine to form functional complexes, e.g., which may be useful for binding ligand or preparing antibodies. These will have substantial diagnostic uses, including detection or quantitation. The functional linkage of the receptor with the p40/IL-B30 ligand provides important insights into the clinical indications that the receptor will be useful for. Thus, antagonists and agonists will have predicted functional effects.

III. Nucleic Acids

This invention contemplates use of isolated nucleic acid or fragments, e.g., which encode these or closely related proteins, or fragments thereof, e.g., to encode a corresponding polypeptide, preferably one which is biologically active. In addition, this invention covers isolated or recombinant DNAs which encode combinations of such proteins or polypeptides having characteristic sequences, e.g., of the DCRS5 SEQ ID NO:2) alone or in combination with others such as an IL-12Rβ1 (see Showe, et al. (1996) Ann. N.Y. Acad. Sci. 795:413–425; Gately, et al. (1998) Ann. Rev. Immunol. 16:495–521; GenBank U03187, NM_005535) subunit. Typically, the nucleic acid is capable of hybridizing, under appropriate conditions, with a nucleic acid sequence segment shown in SEQ ID NO:1, but preferably not with a corresponding segment of other receptors, SEQ ID NOs:3 or 4. Said biologically active protein or polypeptide can be a full length protein, or fragment, and will typically have a segment of amino acid sequence highly homologous, e.g., exhibiting significant stretches of identity, SEQ ID NO:2. Further, this invention covers the use of isolated or recombinant nucleic acid, or fragments thereof, which encode proteins having fragments which are equivalent to the DCRS5 proteins, e.g., intracellular portions. The isolated nucleic acids can have the respective regulatory sequences in the 5' and 3' flanks, e.g., promoters, enhancers, poly-A addition signals, and others from the natural gene. Combinations, as described, are also provided, e.g., combining the DCRS5 with the IL-12β1, or their extracellular ligand binding portions as ligand antagonists. Diagnostic utilities are also clearly important, e.g., of polymorphic or other variants.

An "isolated" nucleic acid is a nucleic acid, e.g., an RNA, DNA, or a mixed polymer, which is substantially pure, e.g., separated from other components which naturally accompany a native sequence, such as ribosomes, polymerases, and flanking genomic sequences from the originating species. The term embraces a nucleic acid sequence which has been removed from its naturally occurring environment, and includes recombinant or cloned DNA isolates, which are thereby distinguishable from naturally occurring compositions, and chemically synthesized analogs or analogs biologically synthesized by heterologous systems. A substantially pure molecule includes isolated forms of the molecule, either completely or substantially pure.

An isolated nucleic acid will generally be a homogeneous composition of molecules, but will, in some embodiments, contain heterogeneity, preferably minor. This heterogeneity is typically found at the polymer ends or portions not critical to a desired biological function or activity.

A "recombinant" nucleic acid is typically defined either by its method of production or its structure. In reference to its method of production, e.g., a product made by a process, the process is use of recombinant nucleic acid techniques, e.g., involving human intervention in the nucleotide sequence. Typically this intervention involves in vitro manipulation, although under certain circumstances it may involve more classical animal breeding techniques. Alternatively, it can be a nucleic acid made by generating a sequence comprising fusion of two fragments which are not naturally contiguous to each other, but is meant to exclude products of nature, e.g., naturally occurring mutants as found in their natural state. Thus, e.g., products made by transforming cells with an unnaturally occurring vector is encompassed, as are nucleic acids comprising sequence derived using any synthetic oligonucleotide process. Such a process is often done to replace, e.g., a codon with a redundant codon encoding the same or a conservative amino acid, while typically introducing or removing a restriction enzyme sequence recognition site, or for some structure-function analysis. Alternatively, the process is performed to join together nucleic acid segments of desired functions to generate a single genetic entity comprising a desired combination of functions not found in the commonly available natural forms, e.g., encoding a fusion protein. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. This will include a dimeric repeat or fusion of the DCRS5 (SEQ ID NOs:1 or 2) with IL-12Rβ1 subunit. Specifically included are synthetic nucleic acids which, by genetic code redundancy, encode equivalent polypeptides to fragments of DCRS5 and fusions of sequences from various different related molecules, e.g., other cytokine family members.

A "fragment" in a nucleic acid context is a contiguous segment of at least about 17 nucleotides, generally at least 21 nucleotides, more generally at least 25 nucleotides, ordinarily at least 30 nucleotides, more ordinarily at least 35 nucleotides, often at least 39 nucleotides, more often at least 45 nucleotides, typically at least 50 nucleotides, more typically at least 55 nucleotides, usually at least 60 nucleotides, more usually at least 66 nucleotides, preferably at least 72 nucleotides, more preferably at least 79 nucleotides, and in particularly preferred embodiments will be at least 85 or more nucleotides, including 90, 100, 120, 140, 160, 180, 200, etc. Typically, fragments of different genetic sequences can be compared to one another over appropriate length stretches, particularly defined segments such as the domains described below.

A nucleic acid which codes for the DCRS5 (SEQ ID NO:2) will be particularly useful to identify genes, mRNA, and cDNA species which code for itself or closely related proteins, as well as DNAs which code for polymorphic, allelic, or other genetic variants, e.g., from different individuals or related species. Preferred probes for such screens are those regions of the receptor which are conserved between different polymorphic variants or which contain nucleotides which lack specificity, and will preferably be full length or nearly so. In other situations, polymorphic variant specific sequences will be more useful. Combinations of polymorphic variants of DCRS5 with variants of IL-12Rβ1 may also be diagnosed.

This invention further covers recombinant nucleic acid molecules and fragments having a nucleic acid sequence identical to or highly homologous to the isolated DNA set forth herein. In particular, the sequences will often be operably linked to DNA segments which control transcription, translation, and DNA replication. These additional segments typically assist in expression of the desired nucleic acid segment.

Homologous, or highly identical, nucleic acid sequences, when compared to one another, e.g., DCRS5 sequences, exhibit significant similarity. The standards for homology in nucleic acids are either measures for homology generally used in the art by sequence comparison or based upon hybridization conditions. Comparative hybridization conditions are described in greater detail below.

Substantial identity in the nucleic acid sequence comparison context means either that the segments, or their complementary strands, when compared, are identical when optimally aligned, with appropriate nucleotide insertions or deletions, in at least about 60% of the nucleotides, generally at least 66%, ordinarily at least 71%, often at least 76%, more often at least 80%, usually at least 84%, more usually at least 88%, typically at least 91%, more typically at least about 93%, preferably at least about 95%, more preferably at least about 96 to 98% or more, and in particular embodiments, as high at about 99% or more of the nucleotides, including, e.g., segments encoding structural domains or other segments described. Alternatively, substantial identity will exist when the segments will hybridize under selective hybridization conditions, to a strand or its complement, typically using a sequence derived from SEQ ID NO:1. Typically, selective hybridization will occur when there is at least about 55% homology over a stretch of at least about 14 nucleotides, more typically at least about 65%, preferably at least about 75%, and more preferably at least about 90%. See, Kanehisa (1984) Nucl. Acids Res. 12:203–213, which is incorporated herein by reference. The length of homology comparison, as described, may be over longer stretches, and in certain embodiments will be over a stretch of at least about 17 nucleotides, generally at least about 20 nucleotides, ordinarily at least about 24 nucleotides, usually at least about 28 nucleotides, typically at least about 32 nucleotides, more typically at least about 40 nucleotides, preferably at least about 50 nucleotides, and more preferably at least about 75 to 100 or more nucleotides. This includes, e.g., 125, 150, 175, 200, 225, 250, 275, 300, 325, 350, etc., and other lengths.

Stringent conditions, in referring to homology in the hybridization context, will be stringent combined conditions of salt, temperature, organic solvents, and other parameters typically controlled in hybridization reactions. Stringent temperature conditions will usually include temperatures in excess of about 30° C., more usually in excess of about 37° C., typically in excess of about 45° C., more typically in excess of about 55° C., preferably in excess of about 65° C., and more preferably in excess of about 70° C. Stringent salt conditions will ordinarily be less than about 500 mM, usually less than about 400 mM, more usually less than about 300 mM, typically less than about 200 mM, preferably less than about 100 mM, and more preferably less than about 80 mM, even down to less than about 50 or 20 mM.

However, the combination of parameters is much more important than the measure of any single parameter. See, e.g., Wetmur and Davidson (1968) J. Mol. Biol. 31:349–370, which is hereby incorporated herein by reference.

The isolated DNA can be readily modified by nucleotide substitutions, nucleotide deletions, nucleotide insertions, and inversions of nucleotide stretches. These modifications result in novel DNA sequences which encode this protein or its derivatives. These modified sequences can be used to produce mutant proteins (muteins) or to enhance the expression of variant species. Enhanced expression may involve gene amplification, increased transcription, increased translation, and other mechanisms. Such mutant DCRS5 inition of the DCRS5 as set forth above, but having an amino acid sequence which differs from that of other cytokine receptor-like proteins as found in nature, whether by way of deletion, substitution, or insertion. In particular, "site specific mutant DCRS5" encompasses a protein having substantial sequence identity with a protein of Table 1, and typically shares most of the biological activities or effects of the forms disclosed herein. Various natural polymorphic variant sequences will also be identified.

Although site specific mutation sites are predetermined, mutants need not be site specific. Mammalian DCRS5 (SEQ ID NOs:1 or 2) mutagenesis can be achieved by making amino acid insertions or deletions in the gene, coupled with expression. Substitutions, deletions, insertions, or many combinations may be generated to arrive at a final construct. Insertions include amino- or carboxy terminal fusions. Random mutagenesis can be conducted at a target codon and the expressed mammalian DCRS5 mutants can then be screened for the desired activity, providing some aspect of a structure-activity relationship. Methods for making substitution mutations at predetermined sites in DNA having a known sequence are well known in the art, e.g., by M13 primer mutagenesis. See also Sambrook, et al. (1989) and Ausubel, et al. (1987 and periodic Supplements). Particularly useful constructs will be extracellular portions of the DCRS5 (SEQ ID NOs:1 or 2) associated with IL-12Rβ1 segments.

The mutations in the DNA normally should not place coding sequences out of reading frames and preferably will not create complementary regions that could hybridize to produce secondary mRNA structure such as loops or hairpins.

The phosphoramidite method described by Beaucage and Carruthers (1981) Tetra. Letts. 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Polymerase chain reaction (PCR) techniques can often be applied in mutagenesis. Alternatively, mutagenesis primers are commonly used methods for generating defined mutations at predetermined sites. See, e.g., Innis, et al. (eds. 1990) PCR Protocols: A Guide to Methods and Applications Academic Press, San Diego, Calif.; and Dieffenbach and Dveksler (1995; eds.) PCR Primer: A Laboratory Manual Cold Spring Harbor Press, CSH, N.Y.

Certain embodiments of the invention are directed to combination compositions comprising the receptor sequences described. In other embodiments, functional portions of the sequences may be joined to encode fusion proteins. In other forms, variants of the described sequences may be substituted.

IV. Proteins, Peptides

As described above, the present invention encompasses primate DCRS5, e.g., whose sequences are disclosed in Table 1, and described above. Allelic and other variants are also contemplated, including, e.g., fusion proteins combining portions of such sequences with others, including, e.g., IL-12Rβ1, epitope tags, and functional domains.

The present invention also provides recombinant proteins, e.g., heterologous fusion proteins using segments from these primate or rodent proteins. A heterologous fusion protein is a fusion of proteins or segments which are naturally not normally fused in the same manner. Thus, the fusion product of a DCRS5 with another cytokine receptor is a continuous protein molecule having sequences fused in a typical peptide linkage, typically made as a single translation product and exhibiting properties, e.g., sequence or antigenicity, derived from each source peptide. A similar concept applies to heterologous nucleic acid sequences. Combinations of various designated proteins into complexes are also provided.

In addition, new constructs may be made from combining similar functional or structural domains from other related proteins, e.g., cytokine receptors or Toll-like receptors, including species variants. For example, ligand-binding or other segments may be "swapped" between different new fusion polypeptides or fragments. See, e.g., Cunningham, et al. (1989) Science 243:1330–1336; and O'Dowd, et al. (1988) J. Biol. Chem. 263:15985–15992, each of which is incorporated herein by reference. Thus, new chimeric polypeptides exhibiting new combinations of specificities will result from the functional linkage of receptor-binding specificities. For example, the ligand binding domains from other related receptor molecules may be added or substituted for other domains of this or related proteins. The resulting protein will often have hybrid function and properties. For example, a fusion protein may include a targeting domain which may serve to provide sequestering of the fusion protein to a particular subcellular organelle.

Candidate fusion partners and sequences can be selected from various sequence data bases, e.g., GenBank, c/o IntelliGenetics, Mountain View, Calif.; and BCG, University of Wisconsin Biotechnology Computing Group, Madison, Wis., which are each incorporated herein by reference. In particular, combinations of polypeptide sequences provided in Tables 1 are particularly preferred. Variant forms of the proteins may be substituted in the described combinations.

The present invention particularly provides muteins which bind cytokine-like ligands, and/or which are affected in signal transduction. Structural alignment of human DCRS5 with other members of the cytokine receptor family show conserved features/residues. See Table 1. Alignment of the human DCRS5 (SEQ ID NO:2) sequence with other members of the cytokine receptor family indicates various structural and functionally shared features. See also, Bazan, et al. (1996) Nature 379:591; Lodi, et al. (1994) Science 263:1762–1766; Sayle and Milner-White (1995) TIBS 20:374–376; and Gronenberg, et al. (1991) Protein Engineering 4:263–269.

Substitutions with either mouse sequences or human sequences are particularly preferred. Conversely, conservative substitutions away from the ligand binding interaction regions will probably preserve most signaling activities; and conservative substitutions away from the intracellular domains will probably preserve most ligand binding properties.

"Derivatives" of the primate DCRS5 include amino acid sequence mutants, glycosylation variants, metabolic derivatives and covalent or aggregative conjugates with other chemical moieties. Covalent derivatives can be prepared by linkage of functionalities to groups which are found in the DCRS5 amino acid side chains or at the N termini, e.g., by means which are well known in the art. These derivatives can include, without limitation, aliphatic esters or amides of the carboxyl terminus, or of residues containing carboxyl side chains, O acyl derivatives of hydroxyl group containing residues, and N acyl derivatives of the amino terminal amino acid or amino group containing residues, e.g., lysine or arginine. Acyl groups are selected from the group of alkyl moieties, including C3 to C18 normal alkyl, thereby forming alkanoyl aroyl species.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine.

A major group of derivatives are covalent conjugates of the receptors or fragments thereof with other proteins of polypeptides. These derivatives can be synthesized in recombinant culture such as N terminal fusions or by the use of agents known in the art for their usefulness in cross linking proteins through reactive side groups. Preferred derivatization sites with cross linking agents are at free amino groups, carbohydrate moieties, and cysteine residues.

Fusion polypeptides between the receptors and other homologous or heterologous proteins are also provided. Homologous polypeptides may be fusions between different receptors, resulting in, for instance, a hybrid protein exhibiting binding specificity for multiple different cytokine ligands, or a receptor which may have broadened or weakened specificity of substrate effect. Likewise, heterologous fusions may be constructed which would exhibit a combination of properties or activities of the derivative proteins. Typical examples are fusions of a reporter polypeptide, e.g., luciferase, with a segment or domain of a receptor, e.g., a ligand-binding segment, so that the presence or location of a desired ligand may be easily determined. See, e.g., Dull, et al., U.S. Pat. No. 4,859,609, which is hereby incorporated herein by reference. Other gene fusion partners include glutathione-S-transferase (GST), bacterial β-galactosidase, trpE, Protein A, β-lactamase, alpha amylase, alcohol dehydrogenase, and yeast alpha mating factor. See, e.g., Godowski, et al. (1988) Science 241:812–816. Labeled proteins will often be substituted in the described combinations of proteins. Associations of the DCRS5 with the IL-12Rβ1 are particularly significant, as described.

The phosphoramidite method described by Beaucage and Carruthers (1981) Tetra, Letts. 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity ligands.

Fusion proteins will typically be made by either recombinant nucleic acid methods or by synthetic polypeptide methods. Techniques for nucleic acid manipulation and expression are described generally, for example, in Sambrook, et al. (1989) Molecular Cloning: A Laboratory Manual (2d ed.), Vols. 1 3, Cold Spring Harbor Laboratory, and Ausubel, et al. (eds. 1987 and periodic supplements) Current Protocols in Molecular Biology, Greene/Wiley, New York, which are each incorporated herein by reference. Techniques for synthesis of polypeptides are described, for example, in Merrifield (1963) J. Amer. Chem. Soc. 85:2149–2156; Merrifield (1986) Science 232: 341–347; and Atherton, et al. (1989) Solid Phase Peptide Synthesis: A Practical Approach, IRL Press, Oxford; each of which is incorporated herein by reference. See also Dawson, et al. (1994) Science 266:776–779 for methods to make larger polypeptides.

This invention also contemplates the use of derivatives of a DCRS5 (SEQ ID NO:2) other than variations in amino acid sequence or glycosylation. Such derivatives may involve covalent or aggregative association with chemical moieties. These derivatives generally fall into three classes: (1) salts, (2) side chain and terminal residue covalent modifications, and (3) adsorption complexes, e.g., with cell membranes. Such covalent or aggregative derivatives are useful as immunogens, as reagents in immunoassays, or in purification methods such as for affinity purification of a receptor or other binding molecule, e.g., an antibody. For example, a cytokine ligand can be immobilized by covalent bonding to a solid support such as cyanogen bromide activated Sepharose, by methods which are well known in the art, or adsorbed onto polyolefin surfaces, with or without glutaraldehyde cross linking, for use in the assay or purification of a cytokine receptor, antibodies, or other similar molecules. The ligand can also be labeled with a detectable group, e.g., radioiodinated by the chloramine T procedure, covalently bound to rare earth chelates, or conjugated to another fluorescent moiety for use in diagnostic assays.

A combination, e.g., including a DCRS5, of this invention can be used as an immunogen for the production of antisera or antibodies specific, e.g., capable of distinguishing between other cytokine receptor family members, for the combinations described. The complexes can be used to screen monoclonal antibodies or antigen-binding fragments prepared by immunization with various forms of impure preparations containing the protein. In particular, the term "antibodies" also encompasses antigen binding fragments of natural antibodies, e.g., Fab, Fab2, Fv, etc. The purified DCRS5 can also be used as a reagent to detect antibodies generated in response to the presence of elevated levels of expression, or immunological disorders which lead to antibody production to the endogenous receptor. Additionally, DCRS5 fragments may also serve as immunogens to produce the antibodies of the present invention, as described immediately below. For example, this invention contemplates antibodies having binding affinity to or being raised against the amino acid sequences shown in Table 1, fragments thereof, or various homologous peptides. In particular, this invention contemplates antibodies having binding affinity to, or having been raised against, specific fragments which are predicted to be, or actually are, exposed at the exterior protein surface of the native DCRS5. Complexes of combinations of proteins will also be useful, and antibody preparations thereto can be made.

In certain other embodiments, soluble constructs, e.g., of the extracellular ligand binding segments of the DCRS5 with the IL-12Rβ1 may be binding compositions for the ligand and may be useful as either ligand antagonists, or as antigens to block ligand mediated signaling. Such may be useful either diagnostically, e.g., for histology labeling for ligand, or therapeutically, e.g., as ligand antagonists.

The blocking of physiological response to the receptor ligands may result from the inhibition of binding of the ligand to the receptor, likely through competitive inhibition. Thus, in vitro assays of the present invention will often use antibodies or antigen binding segments of these antibodies, soluble receptor constructs, or fragments attached to solid phase substrates. These assays will also allow for the diagnostic determination of the effects of either ligand binding region mutations and modifications, or other mutations and modifications, e.g., which affect signaling or enzymatic function.

This invention also contemplates the use of competitive drug screening assays, e.g., where neutralizing antibodies to the receptor complexes or fragments compete with a test compound for binding to a ligand or other antibody. In this manner, the neutralizing antibodies or fragments can be used to detect the presence of a polypeptide which shares one or more binding sites to a receptor and can also be used to occupy binding sites on a receptor that might otherwise bind a ligand. Soluble receptor constructs combining the extracellular, or ligand binding, domains of the DCRS5 with the IL-12Rβ1, may be useful antagonists for competitive binding of p40/IL-B30 ligand.

V. Making Nucleic Acids and Protein

DNA which encodes the protein or fragments thereof can be obtained by chemical synthesis, screening cDNA libraries, or by screening genomic libraries prepared from a wide variety of cell lines or tissue samples. Natural sequences can be isolated using standard methods and the sequences provided herein, e.g., SEQ ID NO:1 or 2. Other species counterparts can be identified by hybridization techniques, or by various PCR techniques, combined with or by searching in sequence databases, e.g., GenBank.

This DNA can be expressed in a wide variety of host cells for the synthesis of a full length receptor or fragments which can in turn, for example, be used to generate polyclonal or monoclonal antibodies; for binding studies; for construction and expression of modified ligand binding or kinase/phosphatase domains; and for structure/function studies. Variants or fragments can be expressed in host cells that are transformed or transfected with appropriate expression vectors. These molecules can be substantially free of protein or cellular contaminants, other than those derived from the recombinant host, and therefore are particularly useful in pharmaceutical compositions when combined with a pharmaceutically acceptable carrier and/or diluent. The protein, or portions thereof, may be expressed as fusions with other proteins. Combinations of the described proteins, or nucleic acids encoding them, are particularly interesting.

Expression vectors are typically self replicating DNA or RNA constructs containing the desired receptor gene, its fragments, or combination genes, usually operably linked to suitable genetic control elements that are recognized in a suitable host cell. These control elements are capable of effecting expression within a suitable host. Multiple genes may be coordinately expressed, and may be on a polycistronic message. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently of the host cell.

The vectors of this invention include those which contain DNA which encodes a combination of proteins, as described, or a biologically active equivalent polypeptide. The DNA can be under the control of a viral promoter and can encode a selection marker. This invention further contemplates use of such expression vectors which are capable of expressing eukaryotic cDNAs coding for such proteins in a prokaryotic or eukaryotic host, where the vector is compatible with the host and where the eukaryotic cDNAs are inserted into the vector such that growth of the host containing the vector expresses the cDNAs in question. Usually, expression vectors are designed for stable replication in their host cells or for amplification to greatly increase the total number of copies of the desirable gene(s) per cell. It is not always necessary to require that an expression vector replicate in a host cell, e.g., it is possible to effect transient expression of the protein or its fragments in various hosts using vectors that do not contain a replication origin that is recognized by the host cell. It is also possible to use vectors that cause integration of the protein encoding portions into the host DNA by recombination.

Vectors, as used herein, comprise plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector but all other forms of vectors which serve an equivalent function and which are, or become, known in the art are suitable for use herein. See, e.g., Pouwels, et al. (1985 and Supplements) Cloning Vectors: A Laboratory Manual, Elsevier, N.Y., and Rodriguez, et al. (eds. 1988) Vectors: A Survey of Molecular Cloning Vectors and Their Uses, Buttersworth, Boston, which are incorporated herein by reference.

Transformed cells are cells, preferably mammalian, that have been transformed or transfected with vectors constructed using recombinant DNA techniques. Transformed host cells usually express the desired proteins, but for purposes of cloning, amplifying, and manipulating its DNA, do not need to express the subject proteins. This invention further contemplates culturing transformed cells in a nutrient medium, thus permitting the proteins to accumulate. The proteins can be recovered, either from the culture or, in certain instances, from the culture medium.

For purposes of this invention, nucleic sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and Pichia, and species of the genus Dictyostelium. Higher eukaryotes include established tissue culture cell lines from animal cells, both of non mammalian origin, e.g., insect cells, and birds, and of mammalian origin, e.g., human, primates, and rodents.

Prokaryotic host vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express the receptor or its fragments include, but are not limited to, such vectors as those containing the lac promoter (pUC series); trp promoter (pBR322 trp); Ipp promoter (the pIN series); lambda pP or pR promoters (POTS); or hybrid promoters such as ptac (pDR540). See Brosius, et al. (1988) "Expression Vectors Employing Lambda, and Ipp derived Promoters", in Vectors: A Survey of Molecular Cloning Vectors and Their Uses, (eds. Rodriguez and Denhardt), Buttersworth, Boston, Chapter 10, pp. 205 236, which is incorporated herein by reference.

Lower eukaryotes, e.g., yeasts and Dictyostelium, may be transformed with DCRS5 sequence containing vectors. For purposes of this invention, the most common lower eukaryotic host is the baker's yeast, *Saccharomyces cerevisiae*. It will be used to generically represent lower eukaryotes although a number of other strains and species are also available. Yeast vectors typically consist of a replication origin (unless of the integrating type), a selection gene, a promoter, DNA encoding the receptor or its fragments, and sequences for translation termination, polyadenylation, and transcription termination. Suitable expression vectors for yeast include such constitutive promoters as 3 phosphoglycerate kinase and various other glycolytic enzyme gene promoters or such inducible promoters as the alcohol dehydrogenase 2 promoter or metallothionine promoter. Suitable vectors include derivatives of the following types: self replicating low copy number (such as the YRp series), self replicating high copy number (such as the YEp series); integrating types (such as the YIp series), or mini chromosomes (such as the YCp series).

Higher eukaryotic tissue culture cells are normally the preferred host cells for expression of the functionally active interleukin or receptor proteins. In principle, many higher eukaryotic tissue culture cell lines are workable, e.g., insect baculovirus expression systems, whether from an invertebrate or vertebrate source. However, mammalian cells are preferred. Transformation or transfection and propagation of such cells has become a routine procedure. Examples of useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pCDNA1; pCD, see Okayama, et al. (1985) Mol. Cell Biol. 5:1136 1142; pMClneo PolyA, see Thomas, et al. (1987) Cell 51:503 512; and a baculovirus vector such as pAC 373 orpAC 610.

For secreted proteins and some membrane proteins, an open reading frame usually encodes a polypeptide that consists of a mature or secreted product covalently linked at its N-terminus to a signal peptide. The signal peptide is cleaved prior to secretion of the mature, or active, polypeptide. The cleavage site can be predicted with a high degree of accuracy from empirical rules, e.g., von-Heijne (1986) Nucleic Acids Research 14:4683–4690 and Nielsen, et al. (1997) Protein Eng. 10:1–12, and the precise amino acid composition of the signal peptide often does not appear to be critical to its function, e.g., Randall, et al. (1989) Science 243:1156–1159; Kaiser et al. (1987) Science 235:312–317. The mature proteins of the invention can be readily determined using standard methods.

It will often be desired to express these polypeptides in a system which provides a specific or defined glycosylation pattern. In this case, the usual pattern will be that provided naturally by the expression system. However, the pattern will be modifiable by exposing the polypeptide, e.g., an unglycosylated form, to appropriate glycosylating proteins introduced into a heterologous expression system. For example, the receptor gene may be co-transformed with one or more genes encoding mammalian or other glycosylating enzymes. Using this approach, certain mammalian glycosylation patterns will be achievable in prokaryote or other cells. Expression in prokaryote cells will typically lead to unglycosylated forms of protein.

The source of DCRS5 (SEQ ID NOs:1 or 2) can be a eukaryotic or prokaryotic host expressing recombinant DCRS5, such as is described above. The source can also be a cell line, but other mammalian cell lines are also contemplated by this invention, with the preferred cell line being from the human species.

Now that the sequences are known, the primate DCRS5, fragments, or derivatives thereof can be prepared by conventional processes for synthesizing peptides. These include processes such as are described in Stewart and Young (1984) Solid Phase Peptide Synthesis, Pierce Chemical Co., Rockford, Ill.; Bodanszky and Bodanszky (1984) The Practice of Peptide Synthesis, Springer Verlag, New York; and Bodanszky (1984) The Principles of Peptide Synthesis, Springer Verlag, New York; all of each which are incorporated herein by reference. For example, an azide process, an acid chloride process, an acid anhydride process, a mixed anhydride process, an active ester process (for example, p nitrophenyl ester, N hydroxysuccinimide ester, or cyanomethyl ester), a carbodiimidazole process, an oxidative reductive process, or a dicyclohexylcarbodiimide (DCCD) additive process can be used. Solid phase and solution phase syntheses are both applicable to the foregoing processes. Similar techniques can be used with partial DCRS5 sequences.

The DCRS5 (SEQ ID NO:2) proteins, fragments, or derivatives are suitably prepared in accordance with the above processes as typically employed in peptide synthesis, generally either by a so called stepwise process which comprises condensing an amino acid to the terminal amino acid, one by one in sequence, or by coupling peptide fragments to the terminal amino acid. Amino groups that are not being used in the coupling reaction typically must be protected to prevent coupling at an incorrect location.

If a solid phase synthesis is adopted, the C terminal amino acid is bound to an insoluble carrier or support through its carboxyl group. The insoluble carrier is not particularly limited as long as it has a binding capability to a reactive carboxyl group. Examples of such insoluble carriers include halomethyl resins, such as chloromethyl resin or bromomethyl resin, hydroxymethyl resins, phenol resins, tert alkyloxycarbonylhydrazidated resins, and the like.

An amino group protected amino acid is bound in sequence through condensation of its activated carboxyl group and the reactive amino group of the previously formed peptide or chain, to synthesize the peptide step by step. After synthesizing the complete sequence, the peptide is split off from the insoluble carrier to produce the peptide. This solid phase approach is generally described by Merrifield, et al. (1963) in J. Am. Chem. Soc. 85:2149 2156, which is incorporated herein by reference.

The prepared protein and fragments thereof can be isolated and purified from the reaction mixture by means of peptide separation, e.g., by extraction, precipitation, electrophoresis, various forms of chromatography, immunoaffinity, and the like. The receptors of this invention can be obtained in varying degrees of purity depending upon desired uses. Purification can be accomplished by use of the protein purification techniques disclosed herein, see below, or by the use of the antibodies herein described in methods of immunoabsorbant affinity chromatography. This immunoabsorbant affinity chromatography is carried out by first linking the antibodies to a solid support and then contacting the linked antibodies with solubilized lysates of appropriate cells, lysates of other cells expressing the receptor, or lysates or supernatants of cells producing the protein as a result of DNA techniques, see below.

Generally, the purified protein will be at least about 40% pure, ordinarily at least about 50% pure, usually at least about 60% pure, typically at least about 70% pure, more typically at least about 80% pure, preferable at least about 90% pure and more preferably at least about 95% pure, and in particular embodiments, 97%–99% or more. Purity will usually be on a weight basis, but can also be on a molar basis. Different assays will be applied as appropriate. Individual proteins may be purified and thereafter combined.

VI. Antibodies

Antibodies can be raised to the various mammalian, e.g., primate DCRS5 (SEQ ID NO:2) proteins and fragments thereof, both in naturally occurring native forms and in their recombinant forms, the difference being that antibodies to the active receptor are more likely to recognize epitopes which are only present in the native conformations. Antibodies recognizing epitopes presented by the combination, e.g., functionally, of the DCRS5 with the IL-12Rβ1 are also contemplated. Denatured antigen detection can also be useful in, e.g., Western analysis. Anti-idiotypic antibodies are also contemplated, which would be useful as agonists or antagonists of a natural receptor or an antibody.

Antibodies, including binding fragments and single chain versions, against predetermined fragments of the protein can be raised by immunization of animals with conjugates of the fragments with immunogenic proteins. Monoclonal antibodies are prepared from cells secreting the desired antibody. These antibodies can be screened for binding to normal or defective protein, or screened for agonistic or antagonistic activity. These monoclonal antibodies will usually bind with at least a KD of about 1 mM, more usually at least about 300 µM, typically at least about 100 µM, more typically at least about 30 µM, preferably at least about 10 µM, and more preferably at least about 3 µM or better.

The antibodies, including antigen binding fragments, of this invention can have significant diagnostic or therapeutic value. They can be potent antagonists that bind to the receptor and inhibit binding to ligand or inhibit the ability of the receptor to elicit a biological response, e.g., act on its substrate. They also can be useful as non neutralizing antibodies and can be coupled to toxins or radionuclides to bind producing cells, or cells localized to the source of the interleukin. Further, these antibodies can be conjugated to drugs or other therapeutic agents, either directly or indirectly by means of a linker.

The antibodies of this invention can also be useful in diagnostic applications. As capture or non neutralizing antibodies, they might bind to the receptor without inhibiting ligand or substrate binding. As neutralizing antibodies, they can be useful in competitive binding assays. They will also be useful in detecting or quantifying ligand. They may be used as reagents for Western blot analysis, or for immunoprecipitation or immunopurification of the respective protein. Likewise, nucleic acids and proteins may be immobilized to solid substrates for affinity purification or detection methods. The substrates may be, e.g., solid resin beads or sheets of plastic.

Protein fragments may be joined to other materials, particularly polypeptides, as fused or covalently joined polypeptides to be used as immunogens. Mammalian cytokine receptors and fragments may be fused or covalently linked to a variety of immunogens, such as keyhole limpet hemocyanin, bovine serum albumin, tetanus toxoid, etc. See Microbiology, Hoeber Medical Division, Harper and Row, 1969; Landsteiner (1962) Specificity of Serological Reactions, Dover Publications, New York; and Williams, et al. (1967) Methods in Immunology and Immunochemistry, Vol. 1, Academic Press, New York; each of which are incorporated herein by reference, for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) Basic and Clinical Immunology (4th ed.), Lange Medical Publications, Los Altos, Calif., and references cited therein; Harlow and Lane (1988) Antibodies: A Laboratory Manual, CSH Press; Goding (1986) Monoclonal Antibodies: Principles and Practice (2d ed.) Academic Press, New York; and particularly in Kohler and Milstein (1975) in Nature 256: 495 497, which discusses one method of generating monoclonal antibodies. Each of these references is incorporated herein by reference. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," Science 246:1275–1281; and Ward, et al. (1989) Nature 341:544–546, each of which is hereby incorporated herein by reference. The polypeptides and antibodies of the present invention may be used with or without modification, including chimeric or humanized antibodies.

Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant or chimeric immunoglobulins may be produced, see Cabilly, U.S. Pat. No. 4,816,567; or made in transgenic mice, see Mendez, et al. (1997) Nature Genetics 15:146–156. These references are incorporated herein by reference.

The antibodies of this invention can also be used for affinity chromatography in isolating the DCRS5 proteins or peptides. Columns can be prepared where the antibodies are linked to a solid support, e.g., particles, such as agarose, Sephadex, or the like, where a cell lysate may be passed through the column, the column washed, followed by increasing concentrations of a mild denaturant, whereby the purified protein will be released. Alternatively, the protein may be used to purify antibody. Appropriate cross absorptions or depletions may be applied.

The antibodies may also be used to screen expression libraries for particular expression products. Usually the antibodies used in such a procedure will be labeled with a moiety allowing easy detection of presence of antigen by antibody binding.

Antibodies raised against a cytokine receptor will also be used to raise anti-idiotypic antibodies. These will be useful in detecting or diagnosing various immunological conditions related to expression of the protein or cells which express the protein. They also will be useful as agonists or antagonists of the ligand, which may be competitive receptor inhibitors or substitutes for naturally occurring ligands. Certain antibodies to receptor subunits or combinations may serve as activating antibodies, which may effect signaling thereby serving, e.g., as ligand agonists.

A cytokine receptor protein that specifically binds to or that is specifically immunoreactive with an antibody generated against a defined immunogen, such as an immunogen consisting of the amino acid sequence of SEQ ID NO: 2, is typically determined in an immunoassay. The immunoassay typically uses a polyclonal antiserum which was raised, e.g., to a protein of SEQ ID NO: 2. This antiserum is selected to have low crossreactivity against other cytokine receptor family members, e.g., IL-12β receptor subunit (SEQ ID NO:4) or IL-6 receptor subunit gp 130 (SEQ ID NO:3), preferably from the same species, and any such crossreactivity is removed by immunoprecipitation prior to use in the immunoassay.

In order to produce antisera for use in an immunoassay, the protein, e.g., of SEQ ID NO:2, is isolated as described herein. For example, recombinant protein may be produced in a mammalian cell line. An appropriate host, e.g., an inbred strain of mice such as Balb/c, is immunized with the selected protein, typically using a standard adjuvant, such as Freund's adjuvant, and a standard mouse immunization protocol (see Harlow and Lane, supra). Alternatively, a synthetic peptide derived from the sequences disclosed herein and conjugated to a carrier protein can be used an immunogen. Polyclonal sera are collected and titered against the immunogen protein in an immunoassay, e.g., a solid phase immunoassay with the immunogen immobilized on a solid support. Polyclonal antisera with a titer of $10^4$ or greater are selected and tested for their cross reactivity against other cytokine receptor family members, e.g., gp130 or IL-12Rβ1 using a competitive binding immunoassay such as the one described in Harlow and Lane, supra, at pages 570–573. Preferably at least two cytokine receptor family members are used in this determination. These cytokine receptor family members can be produced as recombinant proteins and isolated using standard molecular biology and protein chemistry techniques as described herein.

Immunoassays in the competitive binding format can be used for the crossreactivity determinations. For example, the protein of SEQ ID NO:2 can be immobilized to a solid support. Proteins added to the assay compete with the binding of the antisera to the immobilized antigen. The ability of the above proteins to compete with the binding of the antisera to the immobilized protein is compared to the proteins, e.g., of gp130 or IL-12Rβ2. The percent crossreactivity for the above proteins is calculated, using standard calculations. Those antisera with less than 10% crossreactivity with each of the proteins listed above are selected and pooled. The cross-reacting antibodies are then removed from the pooled antisera by immunoabsorption with the above-listed proteins.

The immunoabsorbed and pooled antisera are then used in a competitive binding immunoassay as described above to compare a second protein to the immunogen protein (e.g., the DCRS5 like protein of SEQ ID NO:2). In order to make this comparison, the two proteins are each assayed at a wide range of concentrations and the amount of each protein required to inhibit 50% of the binding of the antisera to the immobilized protein is determined. If the amount of the second protein required is less than twice the amount of the protein of the selected protein or proteins that is required, then the second protein is said to specifically bind to an antibody generated to the immunogen.

It is understood that these cytokine receptor proteins are members of a family of homologous proteins that comprise many identified genes. For a particular gene product, such as the DCRS5, the term refers not only to the amino acid sequences disclosed herein, but also to other proteins that are allelic, non-allelic, or species variants. It is also understood that the terms include nonnatural mutations introduced by deliberate mutation using conventional recombinant technology such as single site mutation, or by excising short sections of DNA encoding the respective proteins, or by substituting new amino acids, or adding new amino acids. Such minor alterations typically will substantially maintain the immunoidentity of the original molecule and/or its biological activity. Thus, these alterations include proteins that are specifically immunoreactive with a designated naturally occurring DCRS5 protein. The biological properties of the altered proteins can be determined by expressing the protein in an appropriate cell line and measuring the appropriate effect, e.g., upon transfected lymphocytes. Particular protein modifications considered minor would include conservative substitution of amino acids with similar chemical properties, as described above for the cytokine receptor family as a whole. By aligning a protein optimally with the protein of the cytokine receptors and by using the conventional immunoassays described herein to determine immunoidentity, one can determine the protein compositions of the invention.

Moreover, antibodies against the receptor subunits may serve to sterically block ligand binding to the functional receptor. Such antibodies may be raised to either subunit alone, or to the combination of DCRS5 with IL-12Rβ1. Antibody antagonists would result.

VII. Kits, Diagnosis, and Quantitation

Both naturally ocurring and recombinant forms of the cytokine receptor like molecules of this invention are particularly useful in kits and assay methods. For example, these methods would also be applied to screening for binding activity, e.g., ligands for these proteins. Several methods of automating assays have been developed in recent years so as to permit screening of tens of thousands of compounds per year. See, e.g., a BIOMEK automated workstation, Beckman Instruments, Palo Alto, Calif., and Fodor, et al. (1991) Science 251:767–773, which is incorporated herein by reference. The latter describes means for testing binding by a plurality of defined polymers synthesized on a solid substrate. The development of suitable assays to screen for a ligand or agonist/antagonist homologous proteins can be greatly facilitated by the availability of large amounts of purified, soluble cytokine receptors in an active state such as is provided by this invention.

Purified DCRS5 (SEQ ID NO:2) can be coated directly onto plates for use in the aforementioned ligand screening techniques. However, non neutralizing antibodies to these proteins can be used as capture antibodies to immobilize the respective receptor on the solid phase, useful, e.g., in diagnostic uses.

This invention also contemplates use of DCRS5, fragments thereof, peptides, and their fusion products in a variety of diagnostic kits and methods for detecting the presence of the protein or its ligand. Alternatively, or additionally, antibodies against the molecules may be incorporated into the kits and methods. Typically the kit will have a compartment containing either a DCRS5 peptide or gene segment or a reagent which recognizes one or the other. Typically, recognition reagents, in the case of peptide, would be a receptor or antibody, or in the case of a gene segment, would usually be a hybridization probe. Other kit components may include other proteins or reagents related to the p40, IL-B30, or IL-12Rβ1 polypeptides of the ligand/receptor pairing.

A preferred kit for determining the concentration of DCRS5 in a sample would typically comprise a labeled compound, e.g., ligand or antibody, having known binding affinity for DCRS5, a source of DCRS5 (naturally occurring or recombinant) as a positive control, and a means for separating the bound from free labeled compound, for example a solid phase for immobilizing the DCRS5 in the test sample. Compartments containing reagents, and instructions, will normally be provided. Appropriate nucleic acid or protein containing kits are also provided.

Antibodies, including antigen binding fragments, specific for mammalian DCRS5 or a peptide fragment, or receptor fragments are useful in diagnostic applications to detect the presence of elevated levels of ligand and/or its fragments. Diagnostic assays may be homogeneous (without a separation step between free reagent and antibody-antigen complex) or heterogeneous (with a separation step). Various commercial assays exist, such as radioimmunoassay (RIA), enzyme linked immunosorbent assay (ELISA), enzyme immunoassay (EIA), enzyme multiplied immunoassay technique (EMIT), substrate labeled fluorescent immunoassay (SLFIA) and the like. For example, unlabeled antibodies can be employed by using a second antibody which is labeled and which recognizes the antibody to a cytokine receptor or to a particular fragment thereof. These assays have also been extensively discussed in the literature. See, e.g., Harlow and Lane (1988) Antibodies: A Laboratory Manual, CSH., and Coligan (ed. 1991 and periodic supplements) Current Protocols In Immunology Greene/Wiley, New York.

Anti-idiotypic antibodies may have similar use to serve as agonists or antagonists of cytokine receptors. These should be useful as therapeutic reagents under appropriate circumstances.

Frequently, the reagents for diagnostic assays are supplied in kits, so as to optimize the sensitivity of the assay. For the subject invention, depending upon the nature of the assay, the protocol, and the label, either labeled or unlabeled antibody, or labeled ligand is provided.

This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent, and will contain instructions for proper use and disposal of reagents. Desirably, the reagents are provided as a dry lyophilized powder, where the reagents may be reconstituted in an aqueous medium having appropriate concentrations for performing the assay.

The aforementioned constituents of the diagnostic assays may be used without modification or may be modified in a variety of ways. For example, labeling may be achieved by covalently or non covalently joining a moiety which directly or indirectly provides a detectable signal. In many of these assays, a test compound, cytokine receptor, or antibodies thereto can be labeled either directly or indirectly. Possibilities for direct labeling include label groups: radiolabels such as $^{125}I$, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Both of the patents are incorporated herein by reference. Possibilities for indirect labeling include biotinylation of one constituent followed by binding to avidin coupled to one of the above label groups.

There are also numerous methods of separating the bound from the free ligand, or alternatively the bound from the free test compound. The cytokine receptor can be immobilized on various matrixes followed by washing. Suitable matrices include plastic such as an ELISA plate, filters, and beads. Methods of immobilizing the receptor to a matrix include, without limitation, direct adhesion to plastic, use of a capture antibody, chemical coupling, and biotin avidin. The last step in this approach involves the precipitation of antibody/antigen complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) Clin. Chem. 30(9):1457 1461, and the double antibody magnetic particle separation as described in U.S. Pat. No. 4,659,678, each of which is incorporated herein by reference.

The methods for linking protein or fragments to various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of an cytokine receptor. These sequences can be used as probes for detecting levels of the respective cytokine receptor in patients suspected of having an immunological disorder. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}$P. However, other techniques may also be employed, such as using biotin modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed which can recognize specific duplexes, including DNA duplexes, RNA duplexes, DNA RNA hybrid duplexes, or DNA protein duplexes. The antibodies in turn may be labeled and the assay carried out where the duplex is bound to a surface, so that upon the formation of duplex on the surface, the presence of antibody bound to the duplex can be detected. The use of probes to the novel anti sense RNA may be carried out in conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) Progress in Growth Factor Res. 1:89–97. Detection of polymorphic variations, which may reflect functional receptor signaling differences, may be useful in determining therapeutic strategy. Variations which reflect greater or lesser response to ligand may allow subsetting of responsive/non-responsive patient pools.

VIII. Therapeutic Utility

This invention provides reagents with significant therapeutic value. See, e.g., Levitzki (1996) Curr. Opin. Cell Biol. 8:239–244. The cytokine receptors (naturally occurring or recombinant), fragments thereof, mutein receptors, and antibodies, along with compounds identified as having binding affinity to the receptors or antibodies, should be useful in the treatment of conditions exhibiting abnormal expression of the receptors or their ligands. Such abnormality will typically be manifested by immunological disorders. See WO 01/18051, which is incorporated herein by reference. Additionally, this invention should provide therapeutic value in various diseases or disorders associated with abnormal expression or abnormal triggering of response to the ligand. For example, the p40/IL B30 ligand has been suggested to be involved in development of cell mediated immunity, e.g., anti-tumor activity, mounting of humoral and cellular immunity, and antiviral effects. In particular, the ligand appears to activate NK and T cells. Therapy may be combined with IL-18, IL-12, TNF, IFNγ, radiation/chemo therapy, adjuvants, or antitumor, antiviral, or antifungal compounds.

Conversely, antagonists, which may be combined with antagonists of TNF, IFNγ, IL-18, or IL-12, or with IL-10 or steroids, may be indicated in chronic Th1 mediated diseases, autoimmunity, or transplant and/or rejection situations, multiple sclerosis, psoriasis, chronic inflammatory conditions, rheumatoid arthritis, osteoarthritis, or inflammatory bowel diseases. Antagonists may take the form of antibodies against the receptor subunits, soluble receptor constructs, or antisense nucleic acids to one or more of the the receptor subunits. The matching of the p40/IL-B30 ligand with receptor subunits DCRS5 and IL-12Rβ1 provides insight into indications for use of the agonists and antagonists.

Therapeutically, based on the p40/IL-B30 activities described, antagonists of the cytokine may be effected, e.g., by soluble DCRS5, with or without soluble IL-12Rβ1, or antibodies to either receptor subunit. Antagonists my be useful as inhibitors of undesirable immune or inflammatory responses, to target memory T cells, or in combination with IL-12/IL-12R antagonists, or other anti-inflammatories or immunosuppressants. Clinical indications may be chronic inflammation or transplant situations. Various polymorphisms may enhance or decrease receptor function, and if dominant, might be useful as therapeutics. Identification of such variants may allow subsetting of responsive or nonresponsive patient pools. The reagents may be useful as detecting or labeling reagents or ablative reagents for memory T cells and/or NK cells.

Gene therapy may render desired cell populations response to p40/IL-B30 ligand, e.g., as adjuvants for tumor immunotherapy, to facilitate activation of tumor infiltrating lymphocytes, T cells, or NK cells. Antisense strategies may be applied, e.g., to prevent receptor responsiveness.

Various abnormal conditions are known in cell types shown to produce both IL-12 p40 and/or IL-B30 mRNA by Northern blot analysis. See Berkow (ed.) The Merck Manual of Diagnosis and Therapy, Merck & Co., Rahway, N.J.; Thorn, et al. Harrison's Principles of Internal Medicine, McGraw-Hill, N.Y.; and Weatherall, et al. (eds.) Oxford Textbook of Medicine, Oxford University Press, Oxford. Many other medical conditions and diseases will be responsive to treatment by an agonist or antagonist provided herein. See, e.g., Stites and Terr (eds.; 1991) Basic and Clinical Immunology Appleton and Lange, Norwalk, Conn.; and Samter, et al. (eds.) Immunological Diseases Little, Brown and Co. Other likely indications for treatment include bone remodeling, sexual dysfunction, prevention of neurodegenerative diseases, dementia, stress, and others. These problems should be susceptible to prevention or treatment using compositions provided herein.

Recombinant cytokine receptors, muteins, agonist or antagonist antibodies thereto, or antibodies can be purified and then administered to a patient. These reagents can be combined for therapeutic use with additional active ingredients, e.g., in conventional pharmaceutically acceptable carriers or diluents, along with physiologically innocuous stabilizers and excipients. These combinations can be sterile, e.g., filtered, and placed into dosage forms as by lyophilization in dosage vials or storage in stabilized aqueous preparations. This invention also contemplates use of antibodies or binding fragments thereof which are not complement binding.

Ligand screening using cytokine receptor or fragments thereof can be performed to identify molecules having binding affinity to the receptors. Subsequent biological assays can then be utilized to determine if a putative ligand can provide competitive binding, which can block intrinsic stimulating activity. Receptor fragments can be used as a blocker or antagonist in that it blocks the activity of ligand. Likewise, a compound having intrinsic stimulating activity can activate the receptor and is thus an agonist in that it simulates the activity of ligand, e.g., inducing signaling. This invention further contemplates the therapeutic use of antibodies to cytokine receptors as antagonists.

The quantities of reagents necessary for effective therapy will depend upon many different factors, including means of administration, target site, reagent physiological life, pharmacological life, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds. 1990) Goodman and Gilman's: The Pharmacological Bases of Therapeutics, 8th Ed., Pergamon Press; and Remington's Pharmaceutical Sciences, 17th ed. (1990), Mack Publishing Co., Easton, Pa.; each of which is hereby incorporated herein by reference. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the Merck Index, Merck†& Co., Rahway, N.J. Because of the likely high affinity binding, or turnover numbers, between a putative ligand and its receptors, low dosages of these reagents would be initially expected to be effective. And the signaling pathway suggests extremely low amounts of ligand may have effect. Thus, dosage ranges would ordinarily be expected to be in amounts lower than 1 mM concentrations, typically less than about 10 $\mu$M concentrations, usually less than about 100 nM, preferably less than about 10 pM (picomolar), and most preferably less than about 1 fM (femtomolar), with an appropriate carrier. Slow release formulations, or slow release apparatus will often be utilized for continuous administration.

Cytokine receptors, fragments thereof, and antibodies or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in many conventional dosage formulations. While it is possible for the active ingredient to be administered alone, it is preferable to present it as a pharmaceutical formulation. Formulations comprise at least one active ingredient, as defined above, together with one or more acceptable carriers thereof. Each carrier must be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by methods well known in the art of pharmacy. See, e.g., Gilman, et al. (eds. 1990) Goodman and Gilman's: The Pharmacological Bases of Therapeutics, 8th Ed., Pergamon Press; and Remington's Pharmaceutical Sciences, 17th ed. (1990), Mack Publishing Co., Easton, Pa.; Avis, et al. (eds. 1993) Pharmaceutical Dosage Forms: Parenteral Medications Dekker, N.Y.; Lieberman, et al. (eds. 1990) Pharmaceutical Dosage Forms: Tablets Dekker, N.Y.; and Lieberman, et al. (eds. 1990) Pharmaceutical Dosage Forms: Disperse Systems Dekker, N.Y. The therapy of this invention may be combined with or used in association with other therapeutic agents, particularly agonists or antagonists of other cytokine receptor family members.

IX. Screening

Drug screening using DCRS5 (SEQ ID NO:2) or fragments thereof can be performed to identify compounds having binding affinity to the receptor subunit, including isolation of associated components. Subsequent biological assays can then be utilized to determine if the compound has intrinsic stimulating activity and is therefore a blocker or antagonist in that it blocks the activity of the ligand.

Moreover, matching of the p40/IL-B30 ligand with the functional receptor of DCRS3 with IL-12R$\beta$1, allows screening for antagonists and agonists with a positive signaling control. Small molecule or antobidy screening can be done.

One method of drug screening utilizes eukaryotic or prokaryotic host cells which are stably transformed with recombinant DNA molecules expressing the DCRS5 in combination with another cytokine receptor subunit, e.g., the IL-12R$\beta$1. The signaling is believed to use STAT4. Cells may be isolated which express a receptor in isolation from other functional receptors. Such cells, either in viable or fixed form, can be used for standard antibody/antigen or ligand/receptor binding assays. See also, Parce, et al. (1989) Science 246:243–247; and Owicki, et al. (1990) Proc. Nat'l Acad. Sci. USA 87:4007–4011, which describe sensitive methods to detect cellular responses. Competitive assays are particularly useful, where the cells are contacted and incubated with a labeled receptor or antibody having known binding affinity to the ligand, such as $^{125}$I-antibody, and a test sample whose binding affinity to the binding composition is being measured. The bound and free labeled binding compositions are then separated to assess the degree of ligand binding. The amount of test compound bound is inversely proportional to the amount of labeled receptor binding to the known source. Many techniques can be used to separate bound from free ligand to assess the degree of ligand binding. This separation step could typically involve a procedure such as adhesion to filters followed by washing, adhesion to plastic followed by washing, or centrifugation of the cell membranes. Viable cells could also be used to screen for the effects of drugs on cytokine mediated functions, e.g., STAT4 signaling and others. Some detection methods allow for elimination of a separation step, e.g., a proximity sensitive detection system.

The broad scope of this invention is best understood with reference to the following examples, which are not intended to limit the inventions to the specific embodiments.

EXAMPLES

I. General Methods

Some of the standard methods are described or referenced, e.g., in Maniatis, et al. (1982) Molecular Cloning, A Laboratory Manual, Cold Spring Harbor Laboratory, Cold Spring Harbor Press; Sambrook, et al. (1989) Molecular Cloning: A Laboratory Manual, (2d ed.), vols. 1–3, CSH Press, NY; or Ausubel, et al. (1987 and Supplements) Current Protocols in Molecular Biology, Greene/Wiley, New York. Methods for protein purification include such methods as ammonium sulfate precipitation, column chromatography, electrophoresis, centrifugation, crystallization, and others. See, e.g., Ausubel, et al. (1987 and periodic supplements); Coligan, et al. (ed. 1996) and periodic supplements, Current Protocols In Protein Science Greene/Wiley, New York; Deutscher (1990) "Guide to Protein Purification" in Methods in Enzymology, vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1990) "Purification of Recombinant Proteins with Metal Chelate Absorbent" in Setlow (ed.) Genetic Engineering, Principle and Methods 12:87–98, Plenum Press, N.Y.; and Crowe, et al. (1992) QIAexpress: The High Level Expression & Protein Purification System QUIAGEN, Inc., Chatsworth, Calif.

Computer sequence analysis is performed, e.g., using available software programs, including those from the GCG (U. Wisconsin) and GenBank sources. Public sequence databases were also used, e.g., from GenBank and others.

Many techniques applicable to IL-10 receptors may be applied to the DCRS5, as described, e.g., in U.S. Pat. No. 5,789,192 (IL-10 receptor), which is incorporated herein by reference.

II. Functional Cloning

It was observed that anti-hIL-12Rβ1 antibody blocked responses of human T cells to p40/IL-B30, and the p40/IL-B30 bound to IL-12Rβ1. This suggested that IL-12Rβ1 was one subunit of the receptor complex for p40/IL-B30.

A mouse T cell population was identified which responded to p40/IL-B30 but not to IL-12, and another population which responded to IL-12 but not p40/IL-B30. In addition, it was observed that Ba/F3 cells expressing recombinant mIL-12Rβ1 and mIL-12Rβ2 responded to IL-12, but not to p40/IL-B30. These results collectively indicated that the receptor complex for p40/IL-B30 contained the IL-12Rβ1 and at least one other subunit which was not IL-12Rβ2. Accordingly an expression cloning strategy was devised to isolate this second receptor component.

A cDNA library was prepared from mRNA isolated from Kit225 cells, an IL-2-dependent human T cell line which responds to both IL-12 and p40/IL-B30. The cDNA library was made using a retroviral expression vector, pMX. Ba/F3 cells expressing recombinant hIL-12Rβ1 were infected with this cDNA library, allowed to recover for 3–4 days in IL-3, then washed and plated at ~15,000 cells/well in 96 well plates in medium containing 50 ng/ml hyper-hp40/hIL-B30. See WO 01/18051. Cultures were supplemented every ~5 days with additional hyper-hp40/hIL-B30. After approximately two weeks 5–10% of the wells exhibited cell growth. Cells were recovered from each well, expanded individually in larger cultures on hyper-hp40/hIL-B30, and tested for growth dependence on hyper-hp40/hIL-B30.

Cells which were p40/IL-B30-dependent for growth were analyzed by PCR for retroviral cDNA inserts. Out of more than 40 isolates analyzed, all but one contained cDNAs encoding the novel receptor DCRS5. This candidate human cDNA was cloned in an expression vector and transfected into Ba/F3 cells expressing hIL-12Rβ1. These cells became responsive to p40/IL-B30; thus we concluded that the novel cDNA encoded the desired DCRS5, functionally an IL-B30 receptor subunit.

III. Features of Full-length DCRS5; Chromosomal Localization

The cytoplasmic domain of DCRS5 is not overall closely related to other cytokine receptor cytoplasmic domains, a common observation in this family of molecules. The cytoplasmic domain contains seven tyr residues, at least three of which are part of recognizable SH2-binding motifs: YEDI, YKPQ, and YFPQ. The YEDI motif is similar to identified binding sites for the tyrosine phosphatase shp2. The latter two motifs are very similar to sequences known to bind Stat1/Stat3, or Stat3, respectively. The YKPQ motif, together with nearby flanking sequences, also resembles to a degree the motifs in Stat4 and IL-12Rβ2 which are known to bind Stat1–3. This is consistent with preliminary data suggesting that p40/IL-B30, like IL-12, activates Stat4.

PCR primers derived from the DCRS5 sequence are used to probe a human cDNA library. Sequences may be derived, e.g., from SEQ ID NO:1, preferably those adjacent the ends of sequences. Full length cDNAs for primate, rodent, or other species DCRS5 are cloned, e.g., by DNA hybridization screening of λgt10 phage. PCR reactions are conducted using *T. aquaticus* Taqplus® DNA polymerase (Stratagene) under appropriate conditions.

Chromosome spreads are prepared. In situ hybridization is performed on chromosome preparations obtained from phytohemagglutinin-stimulated human lymphocytes cultured for 72 h. 5-bromodeoxyuridine was added for the final seven hours of culture (60 µg/ml of medium), to ensure a posthybridization chromosomal banding of good quality.

A PCR fragment, amplified with the help of primers, is cloned into an appropriate vector. The vector is labeled by nick-translation with $^3$H. The radiolabeled probe is hybridized to metaphase spreads at final concentration of 200 ng/ml of hybridization solution as described in Mattei, et al. (1985) Hum. Genet. 69:327–331.

After coating with nuclear track emulsion (KODAK NTB2), slides are exposed. To avoid any slipping of silver grains during the banding procedure, chromosome spreads are first stained with buffered Giemsa solution and metaphase photographed. R-banding is then performed by the fluorochrome-photolysis-Giemsa (FPG) method and metaphases rephotographed before analysis.

Similar appropriate methods are used for other species.

IV. Localization of DCRS5 mRNA

Human multiple tissue (Cat# 1, 2) and cancer cell line blots (Cat# 7757-1), containing approximately 2 µg of poly (A)$^+$ RNA per lane, are purchased from Clontech (Palo Alto, Calif.). Probes are radiolabeled with [α-$^{32}$P] dATP, e.g., using the Amersham Rediprime random primer labelling kit (RPN1633). Prehybridization and hybridizations are performed, e.g., at 65° C. in 0.5 M Na$_2$HPO$_4$, 7% SDS, 0.5 M EDTA (pH 8.0). High stringency washes are conducted, e.g., at 65° C. with two initial washes in 2×SSC, 0.1% SDS for 40 min followed by a subsequent wash in 0.1×SSC, 0.1% SDS for 20 min. Membranes are then exposed at −70° C. to X-Ray film (Kodak) in the presence of intensifying screens. More detailed studies by cDNA library Southerns are performed with selected appropriate human DCRS5 clones to examine their expression in hemopoietic or other cell subsets.

Alternatively, two appropriate primers are selected from SEQ ID NO:1. RT-PCR is used on an appropriate mRNA sample selected for the presence of message to produce a cDNA, e.g., a sample which expresses the gene.

Full length clones may be isolated by hybridization of cDNA libraries from appropriate tissues pre-selected by PCR signal. Northern blots can be performed.

Message for genes encoding DCRS5 will be assayed by appropriate technology, e.g., PCR, immunoassay, hybridization, or otherwise. Tissue and organ cDNA preparations are available, e.g., from Clontech, Mountain View, Calif. Identification of sources of natural expression are useful, as described. And the identification of the functional receptor subunit pairing allows for prediction of what cells express the combination of receptor subunits which will result in a physiological responsiveness to each of the cytokine ligands.

For mouse distribution, e.g., Southern Analysis can be performed: DNA (5 µg) from a primary amplified cDNA library was digested with appropriate restriction enzymes to release the inserts, run on a 1% agarose gel and transferred to a nylon membrane (Schleicher and Schuell, Keene, N.Y.).

Samples for mouse mRNA isolation may include: resting mouse fibroblastic L cell line (C200); Braf:ER (Braf fusion to estrogen receptor) transfected cells, control (C201); T cells, TH1 polarized (Mel14 bright, CD4+ cells from spleen, polarized for 7 days with IFN-γ and anti IL-4; T200); T cells, TH2 polarized (Mel14 bright, CD4+ cells from spleen, polarized for 7 days with IL-4 and anti-IFN-γ; T201); T cells, highly TH1 polarized (see Openshaw, et al. (1995) J. Exp. Med. 182:1357–1367; activated with anti-CD3 for 2, 6, 16 h pooled; T202); T cells, highly TH2 polarized (see Openshaw, et al. (1995) J. Exp. Med. 182:1357–1367; activated with anti-CD3 for 2, 6, 16 h pooled; T203); CD44-CD25+ pre T cells, sorted from thymus (T204); TH1 T cell clone D1.1, resting for 3 weeks after last stimulation with antigen (T205); TH1 T cell clone D1.1, 10 μg/ml ConA stimulated 15 h (T206); TH2 T cell clone CDC35, resting for 3 weeks after last stimulation with antigen (T207); TH2 T cell clone CDC35, 10 μg/ml ConA stimulated 15 h (T208); Mel14+ naïve T cells from spleen, resting (T209); Mel14+ T cells, polarized to Th1 with IFN-γ/IL-12/anti-IL-4 for 6, 12, 24 h pooled (T210); Mel14+ T cells, polarized to Th2 with IL-4/anti-IFN-γ for 6, 13, 24 h pooled (T211); unstimulated mature B cell leukemia cell line A20 (B200); unstimulated B cell line CH12 (B201); unstimulated large B cells from spleen (B202); B cells from total spleen, LPS activated (B203); metrizamide enriched dendritic cells from spleen, resting (D200); dendritic cells from bone marrow, resting (D201); monocyte cell line RAW 264.7 activated with LPS 4 h (M200); bone-marrow macrophages derived with GM and M-CSF (M201); macrophage cell line J774, resting (M202); macrophage cell line J774+LPS+anti-IL-10 at 0.5, 1, 3, 6, 12 h pooled (M203); macrophage cell line J774+LPS+IL-10 at 0.5, 1, 3, 5, 12 h pooled (M204); aerosol challenged mouse lung tissue, Th2 primers, aerosol OVA challenge 7, 14, 23 h pooled (see Garlisi, et al. (1995) Clinical Immunology and Immunopathology 75:75–83; X206); Nippostrongulus-infected lung tissue (see Coffman, et al. (1989) Science 245:308–310; X200); total adult lung, normal (O200); total lung, rag-1 (see Schwarz, et al. (1993) Immunodeficiency 4:249–252; O205); IL-10 K.O. spleen (see Kuhn, et al. (1991) Cell 75:263–274; X201); total adult spleen, normal (O201); total spleen, rag-i (O207); IL-10 K.O. Peyer's patches (O202); total Peyer's patches, normal (O210); IL-10 K.O. mesenteric lymph nodes (X203); total mesenteric lymph nodes, normal (O211); IL-10 K.O colon (X203); total colon, normal (O212); NOD mouse pancreas (see Makino, et al. (1980) Jikken Dobutsu 29:1–13; X205); total thymus, rag-1 (O208); total kidney, rag-1 (0209); total heart, rag-1 (O202); total brain, rag-1 O203); total testes, rag-1 O204); total liver, rag-1 O206); rat normal joint tissue O300); and rat arthritic joint tissue (X300).

Samples for human mRNA isolation may include: peripheral blood mononuclear cells (monocytes, T cells, NK cells, granulocytes, B cells), resting (T100); peripheral blood mononuclear cells, activated with anti-CD3 for 2, 6, 12 h pooled (T101); T cell, TH0 clone Mot 72, resting (T102); T cell, TH0 clone Mot 72, activated with anti-CD28 and anti-CD3 for 3, 6, 12 h pooled (T103); T cell, TH0 clone Mot 72, anergic treated with specific peptide for 2, 7, 12 h pooled (T104); T cell, TH1 clone HY06, resting (T107); T cell, TH1 clone HY06, activated with anti-CD28 and anti-CD3 for 3, 6, 12 h pooled (T1 08); T cell, TH1 clone HY06, anergic treated with specific peptide for 2, 6, 12 h pooled (T1 09); T cell, TH2 clone HY935, resting (T110); T cell, TH2 clone HY935, activated with anti-CD28 and anti-CD3 for 2, 7, 12 h pooled (T111); T cells CD4+CD45RO– T cells polarized 27 days in anti-CD28, IL-4, and anti IFN-γ, TH2 polarized, activated with anti-CD3 and anti-CD28 4 h (T116); T cell tumor lines Jurkat and Hut78, resting (T117); T cell clones, pooled AD130.2, Tc783.12, Tc783.13, Tc783.58, Tc782.69, resting (T118); T cell random γδ T cell clones, resting (T119); Splenocytes, resting (B100); Splenocytes, activated with anti-CD40 and IL-4 (B101); B cell EBV lines pooled WT49, RSB, JY, CVIR, 721.221, RM3, HSY, resting (B102); B cell line JY, activated with PMA and ionomycin for 1, 6 h pooled (B103); NK 20 clones pooled, resting (K100); NK 20 clones pooled, activated with PMA and ionomycin for 6 h (K101); NKL clone, derived from peripheral blood of LGL leukemia patient, IL-2 treated (K106); NK cytotoxic clone 640-A30-1, resting (K107); hematopoietic precursor line TF 1, activated with PMA and ionomycin for 1, 6 h pooled (C100); U937 premonocytic line, resting (M100); U937 premonocytic line, activated with PMA and ionomycin for 1, 6 h pooled (M101); elutriated monocytes, activated with LPS, IFNγ, anti-IL-10 for 1, 2, 6, 12, 24 h pooled (M102); elutriated monocytes, activated with LPS, IFNγ, IL-10 for 1, 2, 6, 12, 24 h pooled (M103); elutriated monocytes, activated with LPS, IFNγ, anti-IL-10 for 4, 16 h pooled (M106); elutriated monocytes, activated with LPS, IFNγ, IL-10 for 4, 16 h pooled (M107); elutriated monocytes, activated LPS for 1 h (M108); elutriated monocytes, activated LPS for 6 h (M109); DC 70% CD1a+, from CD34+ GM-CSF, TNFα 12 days, resting (D101); DC 70% CD1 a+, from CD34+ GM-CSF, TNFα 12 days, activated with PMA and ionomycin for 1 hr (D102); DC 70% CD1a+, from CD34+ GM-CSF, TNFα 12 days, activated with PMA and ionomycin for 6 hr (D103); DC 95% CD1a+, from CD34+ GM-CSF, TNFα 12 days FACS sorted, activated with PMA and ionomycin for 1, 6 hr pooled (D104); DC 95% CD14+, ex CD34+ GM-CSF, TNFα 12 days FACS sorted, activated with PMA and ionomycin 1, 6 hr pooled (D1 05); DC CD1a+ CD86+, from CD34+ GM-CSF, TNFα 12 days FAC sorted, activated with PMA and ionomycin for 1, 6 h pooled (K106); DC from monocytes GM-CSF, IL-4 5 days, resting (D107); DC from monocytes GM-CSF, IL-4 5 days, resting (D1 08); DC from monocytes GM-CSF, IL-4 5 days, activated LPS 4, 16 h pooled (DI 09); DC from monocytes GM-CSF, IL-4 5 days, activated TNFα, monocyte supe for 4, 16 h pooled (D110); leiomyoma L11 benign tumor (X101); normal myometrium M5 (O115); malignant leiomyosarcoma GS 1 (X103); lung fibroblast sarcoma line MRC5, activated with PMA and ionomycin for 1, 6 h pooled (C101); kidney epithelial carcinoma cell line CHA, activated with PMA and ionomycin for 1, 6 h pooled (C102); kidney fetal 28 wk male (O100); lung fetal 28 wk male (O101); liver fetal 28 wk male (O102); heart fetal 28 wk male (O103); brain fetal 28 wk male (O104); gallbladder fetal 28 wk male O106); small intestine fetal 28 wk male O107); adipose tissue fetal 28 wk male (O108); ovary fetal 25 wk female (O109); uterus fetal 25 wk female (O 110); testes fetal 28 wk male (O111); spleen fetal 28 wk male (O112); adult placenta 28 wk (O113); and tonsil inflamed, from 12 year old (X100).

Similar samples may isolated in other species for evaluation.

V. Cloning of Species Counterparts of DCRS5

Various strategies are used to obtain species counterparts of the DCRS5, preferably from other primates or rodents. One method is by cross hybridization using closely related species DNA probes. It may be useful to go into evolutionarily similar species as intermediate steps. Another method is by using specific PCR primers based on the identification of blocks of similarity or difference between genes, e.g., areas of highly conserved or nonconserved polypeptide or nucleotide sequence.

Database searches may identify similar sequences and allow production of appropriate probes.

VI. Production of Mammalian DCRS5 (SEQ ID NO:2) Protein

An appropriate, e.g., GST, fusion construct is engineered for expression, e.g., in E. coli. For example, a mouse IGIF pGex plasmid is constructed and transformed into E. coli. Freshly transformed cells are grown, e.g., in LB medium containing 50 µg/ml ampicillin and induced with IPTG (Sigma, St. Louis, Mo.). After overnight induction, the bacteria are harvested and the pellets containing the DCRS5 protein are isolated. The pellets are homogenized, e.g., in TE buffer (50 mM Tris-base pH 8.0, 10 mM EDTA and 2 mM pefabloc) in 2 liters. This material is passed through a microfluidizer (Microfluidics, Newton, Mass.) three times. The fluidized supernatant is spun down on a Sorvall GS-3 rotor for 1 h at 13,000 rpm. The resulting supernatant containing the cytokine receptor protein is filtered and passed over a glutathione-SEPHAROSE column equilibrated in 50 mM Tris-base pH 8.0. The fractions containing the DCRS5-GST fusion protein are pooled and cleaved, e.g., with thrombin (Enzyme Research Laboratories, Inc., South Bend, Ind.). The cleaved pool is then passed over a Q-SEPHAROSE column equilibrated in 50 mM Tris-base. Fractions containing DCRS5 are pooled and diluted in cold distilled $H_2O$, to lower the conductivity, and passed back over a fresh Q-Sepharose column, alone or in succession with an immunoaffinity antibody column.

Fractions containing the DCRS5 protein are pooled, aliquoted, and stored in the −70° C. freezer.

Comparison of the CD spectrum with cytokine receptor protein may suggest that the protein is correctly folded. See Hazuda, et al. (1969) J. Biol. Chem. 264:1689–1693.

VII. Preparation of Antibodies Specific for DCRS5

Inbred Balb/c mice are immunized intraperitoneally with recombinant forms of the protein, e.g., purified DCRS5 or stable transfected NIH-3T3 cells. Animals are boosted at appropriate time points with protein, with or without additional adjuvant, to further stimulate antibody production. Serum is collected, or hybridomas produced with harvested spleens.

Alternatively, Balb/c mice are immunized with cells transformed with the gene or fragments thereof, either endogenous or exogenous cells, or with isolated membranes enriched for expression of the antigen. Serum is collected at the appropriate time, typically after numerous further administrations. Various gene therapy techniques may be useful, e.g., in producing protein in situ, for generating an immune response. Serum or antibody preparations may be cross-absorbed or immunoselected to prepare substantially purified antibodies of defined specificity and high affinity.

Monoclonal antibodies may be made. For example, splenocytes are fused with an appropriate fusion partner and hybridomas are selected in growth medium by standard procedures. Hybridoma supernatants are screened for the presence of antibodies which bind to the DCRS5, e.g., by ELISA or other assay. Antibodies which specifically recognize specific DCRS5 embodiments may also be selected or prepared.

In another method, synthetic peptides or purified protein are presented to an immune system to generate monoclonal or polyclonal antibodies. See, e.g., Coligan (ed. 1991) Current Protocols in Immunology Wiley/Greene; and Harlow and Lane (1989) Antibodies: A Laboratory Manual Cold Spring Harbor Press. In appropriate situations, the binding reagent is either labeled as described above, e.g., fluorescence or otherwise, or immobilized to a substrate for panning methods. Nucleic acids may also be introduced into cells in an animal to produce the antigen, which serves to elicit an immune response. See, e.g., Wang, et al. (1993) Proc. Nat'l. Acad. Sci. 90:4156–4160; Barry, et al. (1994) BioTechniques 16:616–619; and Xiang, et al. (1995) Immunity 2: 129–135.

VIII. Production of Fusion Proteins with DCRS5 (SEQ ID NOs:1 or 2)

Various fusion constructs are made with DCRS5, including embodiments combining such with IL-12Rβ1 sequence. A portion of the appropriate gene is fused to an epitope tag, e.g., a FLAG tag, or to a two hybrid system construct. See, e.g., Fields and Song (1989) Nature 340:245–246.

The epitope tag may be used in an expression cloning procedure with detection with anti-FLAG antibodies to detect a binding partner, e.g., ligand for the respective cytokine receptor. The two hybrid system may also be used to isolate proteins which specifically bind to DCRS5.

IX. Structure Activity Relationship

Information on the criticality of particular residues is determined using standard procedures and analysis. Standard mutagenesis analysis is performed, e.g., by generating many different variants at determined positions, e.g., at the positions identified above, and evaluating biological activities of the variants. This may be performed to the extent of determining positions which modify activity, or to focus on specific positions to determine the residues which can be substituted to either retain, block, or modulate biological activity.

Alternatively, analysis of natural variants can indicate what positions tolerate natural mutations. This may result from populational analysis of variation among individuals, or across strains or species. Samples from selected individuals are analyzed, e.g., by PCR analysis and sequencing. This allows evaluation of population polymorphisms.

X. Coexpression of DCRS5 and IL-12Rβ1

A vector, or vectors, encoding the respective genes may be transfected into a cell. Preferably, such vector will have selection markers to identify which cells have successfully been transformed. Coexpression of the two genes will allow the gene products to properly associate to form active receptor complexes.

Alternatively, use of methods causing association of functional dimers are available. See, e.g., O'Shea, et al. (1989) Science 245:646–648; Kostelny, et al. (1992) J. Immunol. 148:1547–1553; and Patel, et al. (1996) J. Biol. Chem. 271:30386–30391. Expression of extracellular domains, and physical association, e.g., driven by Fos/Jun leucine zipper affinity, will result in ligand binding constructs which should act as binding compounds for diagnostic or therapeutic uses.

All citations herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

What is claimed is:

1. A binding composition comprising an antigen binding fragment of an antibody which specifically binds to an antigenic polypeptide of SEQ ID NO: 2.

2. The binding composition of claim 1, wherein the binding composition is:
   a) a polyclonal antibody;
   b) a monoclonal antibody; or
   c) an Fab, Fab2, or Fv fragment.

3. The binding composition of claim 1, wherein the antigenic polypeptide comprises:
   a) residues 1–101 of SEQ ID NO: 2;
   b) residues 102–195 of SEQ ID NO: 2;
   c) residues 196–297 of SEQ ID NO: 2;
   d) residues 1–328 of SEQ ID NO: 2; or
   e) residues 1–606 of SEQ ID NO: 2.

4. The binding composition of claim 3, wherein the binding composition is:

a) a polyclonal antibody;
b) a monoclonal antibody;
c) an Fab, Fab2, or Fv fragment; or
d) a humanized antibody.

5. A kit comprising the binding composition of claim 1 and instructions for use.

* * * * *